(12) United States Patent
Rubio Royo et al.

(10) Patent No.: US 8,492,411 B2
(45) Date of Patent: Jul. 23, 2013

(54) 5-(4-METHANESULFONYL-PHENYL)-THIAZOLE DERIVATIVES FOR THE TREATMENT OF ACUTE AND CHRONIC INFLAMMATORY DISEASES

(75) Inventors: Victor Rubio Royo, Leioa-Vizcaya (ES); Antonio De La Hera Martinez, Leioa-Vizcaya (ES); Melchor Alvarez De Mon Soto, Leioa-Vizcaya (ES); Ana Munoz Munoz, Leioa-Vizcaya (ES)

(73) Assignee: Faes Farma, S.A., Leiao-Vizcaya (ES)

( * ) Notice: Subject to any disclaimer, the term of this patent is extended or adjusted under 35 U.S.C. 154(b) by 0 days.

(21) Appl. No.: 12/838,439

(22) Filed: Jul. 17, 2010

(65) Prior Publication Data

US 2010/0305164 A1 Dec. 2, 2010

Related U.S. Application Data

(62) Division of application No. 12/139,661, filed on Jun. 16, 2008, now Pat. No. 7,781,594.

(51) Int. Cl.
*A61K 31/44* (2006.01)

(52) U.S. Cl.
USPC ........................................... 514/342

(58) Field of Classification Search
None
See application file for complete search history.

(56) References Cited

U.S. PATENT DOCUMENTS

| 5,124,342 A | 6/1992 | Kerdesky et al. |
| 2009/0312376 A1 | 12/2009 | Rubio Royo et al. |

OTHER PUBLICATIONS

Jin et al (Acta Pharmacologica Sinica 31:1133-1140, 2010).*
Doan, J. et al., "Rheumatoid Arthritis: An Overview of New and Emerging Therapies", "J. Clin. Pharmacol.", Jul. 2005, pp. 751-762, vol. 45, No. 7.
Lee, D. et al., "Rheumatoid arthritis", "Lancer", Sep. 15, 2001, pp. 903-911, vol. 358, No. 9285.
Souillac, P. et al. , "Differential Scanning Calorimetry in Encyclopedia of Controlled Drug Delivery", "Characterization of Delivery Systems", 1999, Publisher: John Wiley and Sons.
Vippagunta, S. et al., "Crystalline solids", "Advanced Drug Delivery Reviews", 2001, pp. 3-26, vol. 48.
Voll, R. et al., "Do We Need New Treatment That Goes beyond Tumor Necrosis Factor Blockers for Rheumatoid Arthritis?", "Annals New York Academy of Sciences", 2005, pp. 799-810, vol. 1051.
Kerdesky, F., et al., "4-Hydroxythiazole Inhibitors of 5-Lipoxygenase", "Journal of Medicinal Chemistry", Jul. 1991, pp. 2158-2165, vol. 34, No. 7.
Office Action issued Nov. 2, 2012 by Chinese Intellectual Property Office in corresponding Chinese Patent Application Application No. 200980122682.0, including English language translation thereof.

* cited by examiner

*Primary Examiner* — Craig Ricci
(74) *Attorney, Agent, or Firm* — Hultquist, PLLC; Steven J. Hultquist; Mary B. Grant

(57) ABSTRACT

A compound of formula (I):

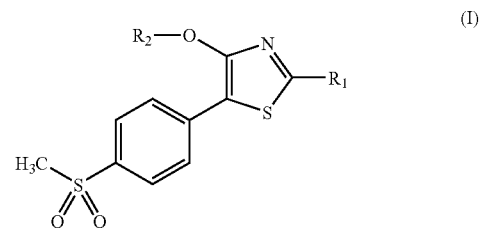

or a pharmaceutically acceptable salt, prodrug and/or solvate thereof, and a method for the treatment of an acute or chronic inflammatory disease by inhibiting the production of at least one pro-inflammatory cytokine selected from TNF-alpha, IFN-gamma, IL-8 and IL-10, involving administering to a patient in need of such treatment a therapeutically effective amount of a compound of formula (I) as defined above.

7 Claims, 7 Drawing Sheets

* Significant values (p<0.05) vs the vehicle

* Significant values(p<0.05) vs the vehicle

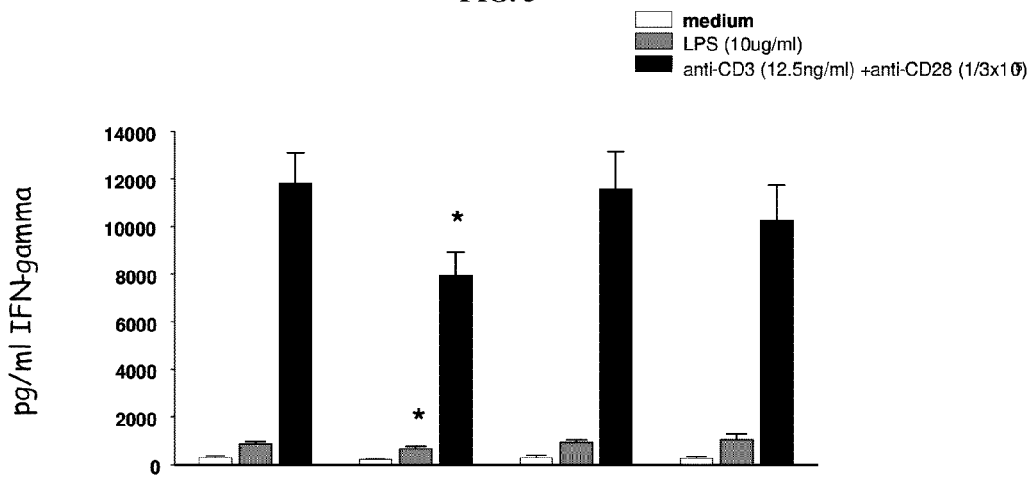
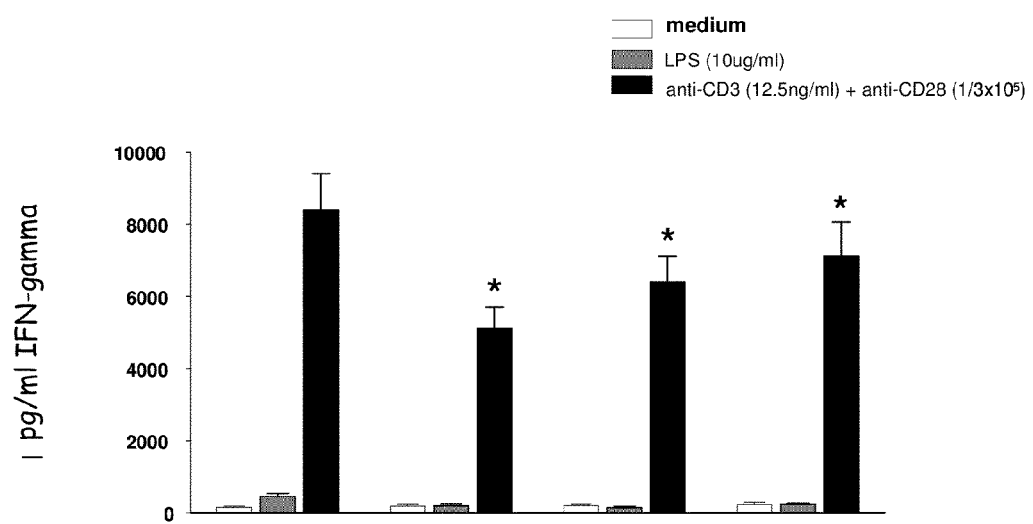

* Significant values (p<0.05) vs the vehicle

* Significant values (p<0.05) vs the vehicle

* Significant values (p<0.05) vs the vehicle

* Significant values (p<0.05) vs the vehicle

5-(4-METHANESULFONYL-PHENYL)-THIAZOLE DERIVATIVES FOR THE TREATMENT OF ACUTE AND CHRONIC INFLAMMATORY DISEASES

CROSS REFERENCE TO RELATED APPLICATION

This is a divisional application and claims priority under 35 USC 120 of U.S patent application Ser. No. 12/139,661 filed on Jun. 16, 2008 now U.S. Pat. No. 7,781,594 in the names of Victor Rubio Royo, et al. for "5-(4.-METHANESULFO-NYL-PHENYL)-THIAZOLE DERIVATIVES FOR THE TREATMENT OF ACUTE AND CHRONIC INFLAMMATORY DISEASES," and subsequently issued as U.S. Pat. No. 7,781,594 on Aug. 24, 2010. The disclosure of U.S. patent application Ser. No. 12/139,661 is hereby incorporated herein by reference in its entirety, for all purposes.

FIELD OF THE INVENTION

The present invention relates to compounds derived from 5-(4-methanesulfonyl-phenyl)-thiazole, their method of synthesis and its use in the preparation of a medicinal product for the treatment and/or prophylaxis of acute and chronic inflammatory diseases or conditions, such as rheumatoid arthritis.

STATE OF THE ART

Immunology is the scientific study of the discrimination between self and non-self. The breakdown of tolerance to self is in the origin of auto-immune diseases. Moreover, other conditions such as transplantation, atherosclerosis, septic and nonseptic acute and chronic inflammatory pathologies and many others diseases, up to now not considered as auto-immune, exhibit immune cell-mediated pathogenic mechanisms. Activation of immune inflammatory effector responses is considered by most authors as being based on two signals:

Signal 1 implies the triggering of the clonal antigen's receptor (TCR-CD3 T-cell receptor complex), that recognize the cognate antigen embebed in the Major Histocompatibility Complex (MHC) molecules. In B-cells, extracellular soluble or membrane-bound antigens cross link the Immunoglobulin CD79 (Ig/CD79) clonal receptor complex to deliver the signal 1 to the antibody-secreting lymphocyte lineage.

A second signal, in addition to antigen-delivered signal 1, is required to avoid tolerance by anergy or clonal deletion. Signal 2 is delivered by co-stimulators such as CD86 expressed on the surface of professional antigen-presenting cells (APC), like human monocytes and their differentiation lineage progeny.

In innate immune inflammatory responses, danger signals are promoted by microbial and self-modified antigens or mitogens that trigger Pattern Recognition Receptors (PRR). PRR signalling pathways, such as TLR4 (the receptor for the Gram-negative wall bacteria lipo-polysaccharide or LPS) deliver the expression of high levels of co-stimulatory surface molecules (i.e., CD80 or CD86). In turn, co-stimulatory ligands CD80-CD86 cross link CD28 on the surface of helper T-cells. The combination of signal 1 (i.e., anti-CD3 antibody cross linking) plus signal 2 (i.e., CD28 cross linking by specific antibodies) experimentally mimics the natural conditions of an efficient inflammatory effector immune response. Notably, approved immune suppressor drugs have some troubles to inhibit the activation of pro-inflammatory cytokine cascades under conditions of high levels of co-stimulation. The latter occur in auto-immune diseases and many other severe acute and chronic inflammatory conditions.

APCs are not only crucial for the immune system to decide the class of immune response by deeply influencing the effect or response either towards tolerant annergy or towards apoptosis of the challenged clon, but also can deliver themselves effector immediate immune inflammatory responses. A well documented example is the production and release of high amounts of Tumour Necrosis Factor Alpha (TNF-alpha) by monocytes in cancer patients. In these patients, TNF-alpha promotes an augmented response and activation of the vascular endothelium, with secretion of Interleukin 8 (IL-8) and other pro-inflammatory cytokines as well as pro-coagulant activities. Altogether, TNF-alpha promotes thrombosis and ischaemia with cancer necrosis, which led to the original definition as cachectin or TNF-alpha. However, TNF-alpha is a pleiotropic cytokine involved in many other disease conditions. There is long-standing evidence that, upon monocytes, LPS may trigger the secretion of massive amounts of TNF-alpha which strongly contribute to the development of septic shock. More recently, the production and secretion of inadequately high amounts of TNF-alpha is considered as a therapeutic target in auto-immune inflammatory diseases, such as rheumatoid arthritis, spondiloarthropathies, Crohn's disease, uveitis and psoriasis. Thus, the use of anti-TNF-alpha has currently been broadly considered as a state of the art strategy to deal with those diseases in which the reduction of available levels of bioactive TNF-alpha might contribute to ameliorate the patient's condition.

In this regard, the number of diseases which might be benefied from the treatment with TNF-alpha antagonists is growing rapidly and includes atherosclerosis, metabolic syndrome, encephalitis, viral hepatitis, glomerulonephritis, inadequate inflammatory response to tumours and septic shock as among several others.

In addition to that produced by some somatic cells, there are two major sources of TNF-alpha production, monocytes and T-lymphocytes. In the course of an acquired immune response, exposition of APCs to danger signals under pro-inflammatory instructive scenarios, triggers the secretion of IL-12 p70 (an heterodimer of p35 and p40), being the latter a co-stimulatory molecule that polarizes the cytokine secretion profile of the activated Th-cells towards Th-1 type. Th1-cells exhibit a characteristic cytokine profile in which interferon gamma (IFN-gamma) secretion is a bona fide footprint. These cells do secrete high amounts of TNF-alpha too.

IFN-gamma produced by Th1 promotes many effects that may be relevant in the understanding of inflammatory diseases. On one hand, it increases the level of TNF-alpha secretion by a given stimuli. On the other hand, it promotes a stronger signalling pathway downstream TNF-alpha receptors. Altogether, IFN-gamma in addition to its own direct effects such as anti-viral activity, increases expression in MHC-II and contributes to inflammation and lesions by increasing the still strong effects of TNF-alpha.

The pro-inflammatory cascade initiated by the production of TNF-alpha in monocytes or IFN-gamma and TNF-alpha in Th1-cells, becomes amplified through other pro-inflammatory cytokines pathways such as IL-8. IL-8, in spite of its original name, was described as a chemokine produced by macrophages and other cell types such as epithelial cells, and it is also synthesized by endothelial cells, and accordingly is also be termed CXCL8. While neutrophil granulocytes are the primary target cells of IL-8 there is a relative wide range of cells (endothelial cells, macrophages, mast cells, Keratinocytes) responding to this chemokine, too. Primary function of IL-8 is the induction of chemotaxis in its target cells (e.g. neutrophil granulocytes). In neutrophils series of cell-physiological responses required for migration and its target function phagocytosis are also induced like increase of intracellular Ca2+, exocytosis (e.g. histamine release), respiratory burst. IL-8 can be secreted by any cells with TLRs which are involved in the innate immune response. IL-8's primary function is to recruit neutrophils to phagocytose the antigen which trigger the antigen pattern TLRs. By conveying IL-8 target cells to the endothelium and other target tissues IL-8 is thus implicated in the amplification and execution of many of the TNF-alpha pathogenic roles.

Leucocytes migration and homing are not only regulated by chemokines and their receptors but also by a number of adhesion molecules. Among them, the selectin CD62L is acknowledged as a therapeutic target to prevent leucocytes migration to the lymph nodes and thus is evaluated as a parameter to rank the in vitro effects of non-steroid anti-inflammatory drugs (NSAIDs).

Many immune suppressor and anti-TNF-alpha molecules affect the normal immune defence mechanisms because they promote cytotoxic effects upon immune cells or inhibit the proliferative mechanism that underlie under the clonal expansion preceding the successful effector immune responses.

Given the importance of the extracellular space secreted TNF-alpha, many efforts have been displayed to design therapeutic agents that block the interaction of extracellular TNF-alpha with both TNF-receptor I and/or TNF-receptor II. The most relevant approaches have been the use of soluble decoy TNF-receptor that captures TNF-alpha and thanks to the long time of dissociation prevents the pro-inflammatory ligand interaction with the cellular receptors.

A second strategy has been to produce humanised anti-human TNF-alpha antibodies either conventional or created as bis-specific single chain molecules that target as well other molecules relevant in a given disease (i.e., anti-VEGF/anti-TNF-alpha in rheumatoid arthritis). Whereas the molecules described above are TNF-alpha antagonists, they restrict their mechanism of action to the blockade of extracellular secreted TNF-alpha.

A comprehensive and not exhaustive list of targets that drive to TNF-alpha production and secretion might be: a) molecules driving transcriptional expression of TNF-alpha; b) molecules driving TNF-alpha-RNA transport from the nucleus to the cytoplasm and RNA splicing; c) molecules directing TNF-alpha translation; d) molecules regulating TNF-alpha-mRNA stability; e) molecules directing Golgi vesicles to the membrane where the pro-TNF-alpha surface form is anchored; f) molecules such as TNF-alpha-converting enzyme (TACE) implicated in the secretory shedding of TNF-alpha and g) molecules regulating the internalization of the surface form of pro-TNF-alpha and its signaling. All of these refer to intracellular targets of TNF-alpha production and secretion.

In spite of the different approaches to design therapeutic agents that block the production of TNF-alpha, it would be highly desirable to find new drugs which selectively blocker not only the TNF-alpha production but also the production of another key pro-inflammatory cytokines, as IFN-gamma.

SUMMARY OF THE INVENTION

The authors of the present invention have surprisingly found that compounds of formula (I) have shown a number of highly interesting immune modulating effects potentially useful for the control of the pathogenic mechanisms of acute and chronic inflammatory diseases and therefore, with potential clinical applications. In particular, the compounds used in the invention have been able to inhibit TNF-alpha production by peripheral blood mononuclear cells (PBMC) from patients suffering from a chronic inflammatory disease, such as rheumatoid arthritis, as well as to inhibit IFN-gamma secretion by those cells after T-cells stimulation. Additionally, compounds of formula (I) have been able to inhibit secretion of cytokines IL-8 and IL-10. This whole of immune modulating effects of compounds of formula (I) was not associated to any toxic effect on mononuclear cells from peripheral blood and, moreover, the activation and proliferative response after mitogenic stimuli was not modified by these compounds.

The combination, in only one small molecule, of inhibitory effects on several pro-inflammatory cytokines as TNF-alpha, IFN-gamma and IL-8 of crucial importance in the pathophysiology of systemic and organ-specific autoimmune disorders, transplantation, acute and chronic inflammatory diseases, some metabolic and degenerative diseases and atherosclerosis, allows compounds of formula (I) to belong to a new category of immune modulators for targeting the cascade of pro-inflammatory cytokines at various potentially re-programming levels of clinical and therapeutic relevance.

Notably the immune cells are sessile, and enter organs to patrol the body tissues that infiltrate in the inflamed conditions where they concentrate in the lesions distributed according to the disease activity, target organs and extension of damage. Since the compounds used in the invention are expected to modulate some aspect of the patho-physiological process, then imaging studies can be used to characterize the number of receptors, binding efficiency, receptor occupancy and medicament probe concentration. Given the homing properties of leukocytes, the detection of the therapeutic target brings together information about the location of the target cells and the lesion sites.

Therefore, the compounds of formula (I) also exhibit a potential use as imaging biomarkers in drug development, clinical trials and individualized medicine, which allows to provide information not only on pharmacokinetics, distribution and dosing but also relevant data on the individualized response patterns in preclinical and clinical trials. The latter may lead to the definition of validated, reliable, individualized surrogate biomarkers of clinical endpoints administering to a patient who needs such prognostic and individualized evaluation of effective amount of a compound of formula (I) or a pharmaceutical composition thereof optimized for the distinct bio-imaging technology known by persons skilled in the art.

According to a first aspect, the present invention relates to a compound of formula (I):

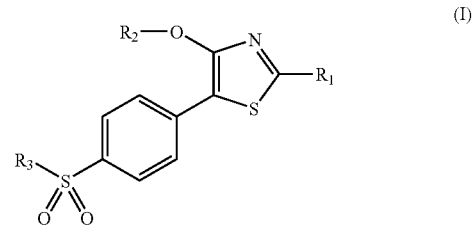

wherein:
R$_1$ is selected from hydrogen, substituted or unsubstituted C$_1$-C$_6$ alkyl, substituted or unsubstituted cycloalkyl, substituted or unsubstituted aryl and substituted or unsubstituted heterocyclyl;

R₂ is selected from hydrogen, substituted or unsubstituted $C_1$-$C_6$ alkyl, substituted or unsubstituted cycloalkyl, and N(R'R") wherein R' and R" are independently hydrogen or $C_1$-$C_6$ alkyl; and R₃ is a $C_1$-$C_6$ alkyl radical, or a pharmaceutically acceptable salt, prodrug and/or solvate thereof.

Another aspect of the present invention is aimed at a pharmaceutical composition comprising a compound of formula (I) as defined above, or a pharmaceutically acceptable salt, prodrug or solvate thereof, and at least one pharmaceutically acceptable carrier, adjuvant and/or vehicle.

Another aspect of the present invention refers to a method for treating an acute or chronic inflammatory disease by inhibiting the production of at least one pro-inflammatory cytokine selected from TNF-alpha, IFN-gamma, IL-8 and IL-10, which comprises administering to a patient who needs such treatment a therapeutically effective amount of a compound of formula (I) as defined above or a pharmaceutical composition thereof.

In a particular aspect of the invention, the acute or chronic inflammatory disease is selected from acute and chronic seropositive or seronegative olygoarthritis and polyarthritis, spondiloarthropathies, glomerulonephritis, colagenopathies, tubulo-interstitial nephritis, metabolic syndrome, atherosclerosis, osteoarthritis, asthma, chronic obstructive pulmonary disease, interstitial lung disease, multiple sclerosis, demyelinating diseases, meningitis, encephalitis, meningoencephalitis, inflammatory radiculopathies and peripheral neuropathies, inflammatory bowel disease, cirrhosis, hepatitis, heart failure, ischemic disease, renal failure, inflammatory cystitis, benign prostatic hyperplasia, prostatitis, myocarditis, pericarditis, uveitis, atopic dermatitis, eccema, urticaria, psoriasis, rosacea, allergic rhinitis, sepsis, septic shock, multiorganic failure, systemic autoimmune diseases such as systemic lupus erythematosus, vasculitis, dermatomyositis, amyloidosis or sarcoidosis, organ specific autoimmune diseases such as myasthenia gravis, thyroiditis or insulinitis, organ transplantation, infectious ant tumor induced inflammation, TNF-alpha dependent cellular degeneration, necrosis, apoptosis, graft versus host disease, cachexia and autocrine and paracrine pathological cell growth.

These therapeutic indications are the consequence of at least an abnormal immune-response, an immune-disregulation, an immune-disturbance, an immune-pathogenesis, an immune-therapy, an immune-suppression or an immune-modulating biological response.

Finally, another aspect of the invention refers to the use of a compound of formula (I) as defined above as imaging biomarker in imaging and pharmaco-imaging technologies, for finding immunological lesions, target cells and target molecules.

BRIEF DESCRIPTION OF THE FIGURES

FIG. 5: Influence on IFN-gamma production in PBMC from healthy volunteers (n=10) by compound 12. Columns represented the mean and standard error of the duplicate cultures performed in each sample in the different experimental conditions. The asterisk represented the statistically significant differences ($p<0.05$) of the corresponding data with respect to the vehicle for the indicated experimental condition.

FIG. 6: Influence on IFN-gamma production in PBMC from patients with rheumatoid arthritis by compound 12. Columns represent the mean and standard error of the duplicate cultures performed in each sample in the different experimental conditions. Asterisks represent statistically significant differences ($p<0.05$) of the corresponding data with respect to the vehicle for each of the different experimental conditions.

DETAILED DESCRIPTION OF THE INVENTION

Figure 1:
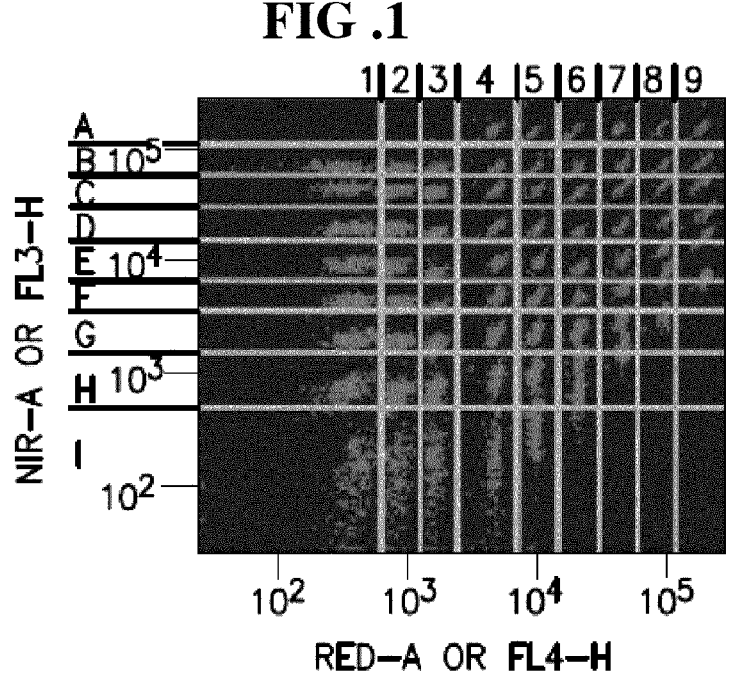
FIG. 1: Different fluorescent features of selected microparticles for the development of Cytometric Bead Array (CBA).

In the context of the present invention, the following terms have the meaning detailed below:

The term "$C_{1-6}$ alkyl" refers to a linear or branched hydrocarbon chain radical consisting of carbon and hydrogen atoms, containing no insaturation, having one to six carbon atoms, and which is attached to the rest of the molecule by a single bond, e.g., methyl, ethyl, n-propyl, i-propyl, n-butyl, t-butyl, n-pentyl, etc. $C_{1-6}$ alkyl radicals may be optionally substituted by one or more substituents such as cycloalkyl, aryl, heterocyclyl, halo, hydroxy, alkoxy, cyano, amino, nitro or alkylthio.

The term "cycloalkyl" refers to a stable 3-to 8-membered ring radical which is saturated or partially saturated, and which consists solely of carbon and hydrogen atoms, such as cyclohexyl or cyclopentyl. Unless otherwise stated specifically in the specification, the term "cycloalkyl" is meant to include cycloalkyl radicals which are optionally substituted by at least one substituent independently selected from the group consisting of hydrogen, $C_{1-6}$ alkyl radical, halo, hydroxyl, —N($R_3$)($R_4$), wherein $R_3$ and $R_4$ are independently selected from hydrogen and linear or branched $C_{1-6}$ alkyl radical.

The term "aryl" refers to a stable 5- to 8-membered aromatic ring radical, and which consists solely of carbon and hydrogen atoms, such as phenyl or cyclooctatetraene. Unless otherwise stated specifically in the specification, the term "aryl" is meant to include aryl radicals which are optionally substituted by at least one substituent independently selected from the group consisting of hydrogen, $C_{1-6}$ alkyl radical, halo, hydroxyl, —N($R_3$)($R_4$), wherein $R_3$ and $R_4$ are independently selected from hydrogen and linear or branched $C_{1-6}$ alkyl radical.

"Heterocyclyl" refers to a stable 3-to 8 membered ring radical which consists of carbon atoms and from one to five heteroatoms selected from the group consisting of nitrogen, oxygen, and sulphur. For the purposes of this invention, the heterocycle may be partially or fully saturated or aromatic. Examples of such heterocycles include, but are not limited to pyrrolidine, pyridine, thiophene, furan, etc. Unless otherwise stated specifically in the specification, the term "heterocyclyl" is meant to include heterocyclyl radicals which are optionally substituted by at least one substituent independently selected from the group consisting of hydrogen, $C_{1-6}$ alkyl radical, halo, hydroxyl, —N($R_3$)($R_4$), wherein $R_3$ and $R_4$ are independently selected from hydrogen and linear or branched $C_{1-6}$ alkyl radical.

The term "halo" refers to bromo, chloro, iodo or fluoro.

The term "acute and chronic seropositive or seronegative olygoarthritis and polyarthritis" refers to diseases with synovitis involving one or several dyarthrodial joints, with either positive or negative rheumatoid factor, including rheumatoid arthritis and both primary and secondary Sjögren syndrome.

The term "spondiloarthropahies" refers to immune pathogenically HLA-B27-associated inflammatory diseases with involvement of sacro-ileal joints and/or spinal and/or peripheral joints, also including uveitis.

The term "glomerulonephritis" refers to inflammatory lesions of the renal glomerulus.

The term "tubulo-interstitial nephritis" refers to inflammatory diseases involving tubules and renal interstitium.

The term "colagenopathies" refers to systemic inflammatory diseases with pathogenic immune mechanism including systemic lupus erythematosus (SLE), dermatomyositis and sclerodermia.

The term "inflammatory bowel disease" refers to inflammatory diseases of the gastrointestinal tract with pathogenic immune mechanism, either with or without systemic features, including Crohn's disease and ulcerative colitis.

The term "obstructive pulmonary disease" refers to bronchial diseases with either reversible or irreversible decrease of the flow expiratory volume (FEY), including asthma and chronic obstructive pulmonary disease.

The term "interstitial lung disease" refers to inflammatory diseases involving lung interstitium.

The term "demyelinating diseases" refers to inflammatory diseases of the central nervous system with an immune pathogenic mechanism provoking myelin lysis, including multiple sclerosis and optical neuritis.

The term "meningitis, encephalitis and meningoencephalitis" refers to inflammatory diseases of the meninges and/or other structures of the central nervous system.

The term "inflammatory radiculopathies and peripheral neuropathies" refers to inflammatory diseases of the peripheral nervous system.

The term "inflammatory cystitis" refers to inflammatory diseases of the bladder.

The term "benign prostatic hyperplasia" refers to nonmalignant hyperthrophy and/or hyperplasia of the prostate.

The term "atopic dermatitis, eccema and urticaria" refers to allergic skin diseases with immune pathogenic mechanism with or without involvement of IgE.

The term "psoriasis" refers to hyperkeratosic and erythematous skin reaction with an immune system pathogenic mechanism.

The term "rosacea" refers to common inflammatory condition of the skin characterised by erythema (flushing and redness) on the central face and across the cheeks, nose or forehead also can also less commonly affect the neck and chest.

The term "allergic rhinitis" refers to intermittent (also called seasonal) or persistent (also called perennial) inflammatory of immune pathogenic mechanism.

The term "sepsis, septic shock and multiorganic failure" refers to systemic inflammatory diseases mediated by an abnormal immune response to microbial agents and other ethiological factors.

The term "sarcoidosis and amyloidosis" refers to idiopathic immunological diseases with organ and/or systemic involvement and no well defined ethiology in which an abnormal immune response can be observed.

The term "organ specific auto-immune diseases" refers to immune system-mediated lesion of organs with no defined ethiological factors, including myastenia gravis, tyroiditis, hypophysitis, adrenalitis and others.

The term "organ transplantation" refers to prevention and treatment of rejection of transplanted cells and organs.

The term "infection and tumour-induced inflammation" refers to abnormal immune responses secondary to microbial agents or cancer stimuli.

The term "TNF-alpha dependent cellular degeneration, apoptosis or necrosis" refers to tissue degeneration or death induced by TNF-alpha.

The term "graft versus host disease" refers to inflammatory immune responses induced by graft cells.

The term "caquexia" refers to systemic anorexia or malnutrition induced by inflammatory or neoplasic diseases.

The term "atherosclerosis" refers to any hardening of arteries secondary to atheroma or accumulation in the artheryl walls that is made up of inflammatory cells (mostly macrophage cells) and cell debris, that contain lipids.

The term "ischemic diseases" refers to lesion of organs secondary to reduced tissue oxigenation and/or blood flow including heart and cerebrovascular ischaemia.

The term "autocrine and paracrine pathological cell growth" refers to malignant or benign diseases with cell use of TNF-alpha as a cytokine regulating activation and proliferation factor for the cells.

Unless otherwise indicated, the compounds of the invention are intended to include compounds that only differ in the presence of one or more isotopically enriched atoms. For example, compounds having the present structures except for the substitution of a hydrogen with deuterium or tritium, or the substitution of a carbon with a $^{13}$C- or $^{14}$C-enriched carbon or a $^{15}$N-enriched nitrogen are within the scope of this invention.

The term "pharmaceutically acceptable salts, solvates or prodrugs thereof" relates to salts, solvates or prodrugs which, when administered to the recipient, can provide (directly or indirectly) a compound such as the one described herein. Nevertheless, it will be observed that pharmaceutically unacceptable salts are also within the scope of the invention because they can be useful for preparing pharmaceutically acceptable salts. Salts, prodrugs and derivatives can be prepared by means of methods known in the state of the art. "Pharmaceutically acceptable" preferably relates to molecular entities and compositions which are physiologically tolerable and do not typically cause an allergic reaction or a similar unfavorable reaction, such as gastric disorders, dizziness and the like, when administered to a human or animal. The term "pharmaceutically acceptable" means that it is approved by a regulatory agency of a federal or state government or is included in the US pharmacopoeia or another generally recognized pharmacopoeia for use in animals, and more particularly in humans.

For example, the pharmaceutically acceptable salts of the compounds described previously herein are synthesized from the previously described compound containing a basic or acidic unit by means of conventional chemical methods. Such salts are generally prepared, for example, by reacting the free acidic or basic forms of these compounds with a stoichiometric amount of the suitable base or acid in water or in an organic solvent or in a mixture of both. Non-aqueous media, such as ether, ethyl acetate, ethanol, isopropanol or acetonitrile, are generally preferred. Examples of acid addition salts include mineral acid addition salts such as hydrochloride, hydrobromide, hydroiodide, sulfate, nitrate, phosphate, for example, and organic acid addition salts such as acetate, maleate, fumarate, citrate, oxalate, succinate, tartrate, malate, mandelate, methanesulfonate and p-toluenesulfonate, for example. Examples of alkaline addition salts include inorganic salts such as sodium, potassium, calcium, ammonium, magnesium, aluminium and lithium, for example, and organic alkaline salts such as ethylenediamine, ethanolamine, N,N-dialkylenethanolamine, glucamine and basic amino acid salts for example.

The term "prodrug" is defined herein as a chemical compound which has undergone a chemical derivation such as a substitution or addition of an additional chemical group in order to change (for pharmaceutical use) some of its physical chemistry properties, such as solubility or bioavailability, for example an ester or ether derived from an active compound giving an active compound per se after the administration to a subject. Examples of well known methods for producing a prodrug from a given active compound are known by persons skilled in the art and can be found in Krogsgaard-Larsen et al., Textbook of Drug Design and Discovery, Taylor & Francis (April 2002), for example. According to this invention, the term "solvate" is understood to mean any form of a compound of the invention having another molecule (most likely a polar solvent) bound to it through a non-covalent bond. Examples of solvates include hydrates and alcoholates, for example methanolate.

Particularly preferred prodrugs are those increasing the bioavailability of the compounds of this invention when such compounds are administered to a patient (allowing an orally administered compound to be more quickly absorbed into the blood, for example) or those increasing the distribution of the original compound to a biological compartment (the brain or the lymphatic system, for example) with respect to the original species.

The compounds of the invention may be in crystalline form, i.e. as polymorphs, either as free compounds or as solvates (hydrates, for example) and it is understood that both forms are within the scope of the present invention. Solvation methods are generally known in the art. Suitable solvates are pharmaceutically acceptable solvates. In a particular embodiment, the solvate is a hydrate.

Salts, solvates and prodrugs can be prepared by means of methods known in the state of the art. It will be observed that pharmaceutically unacceptable salts, solvates or prodrugs are also included within the scope of the invention because they can be useful in the preparation of pharmaceutically acceptable salts, solvates or prodrugs.

The compounds of formula (I) or their salts or solvates are preferably in pharmaceutically acceptable form or in substantially pure form. A pharmaceutically acceptable form is understood, inter alia, as having a pharmaceutically acceptable purity level, excluding normal pharmaceutical additives such as diluents and excipients, and without including any material considered to be toxic at normal dosage levels. The purity levels for the drug are preferably above 50%, more preferably above 70%, and still more preferably above 90%. In a preferred embodiment, it is above 95% of the compound of formula (I), or of its salts, solvates or prodrugs.

The compounds of the invention shown by the formula (I) described above can include enantiomers depending on the presence of chiral centers or isomers depending on the presence of multiple bonds (for example, Z, E). The individual isomers, enantiomers, diastereoisomers and mixtures thereof are within the scope of the present invention.

In a particular embodiment, for its use in imaging and pharmaco-imaging technologies, or their displacement as biomarkers in drug development, clinical trials, and individualized medicine, the compound of formula (I) may be labeled with fluorescent or luminiscent tags or flags, introducing the markers by any method known by a skilled person in the art.

In a particular embodiment of the invention, $R_1$ is a substituted or unsubstituted $C_1$-$C_6$ alkyl. Preferably $R_1$ is methyl.

In another particular embodiment, $R_2$ is hydrogen, substituted or unsubstituted $C_1$-$C_6$ alkyl, substituted or unsubstituted cycloalkyl. Preferably, $R_2$ is a substituted or unsubstituted cycloalkyl. More preferably, $R_2$ is cyclopentyl.

In a still another particular embodiment, $R_3$ is methyl.

In another still more particular embodiment, the compound of formula (I) used in the present invention is selected from the following compounds:

(1)
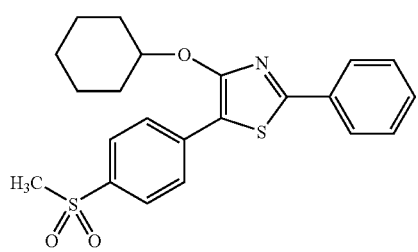
(2)
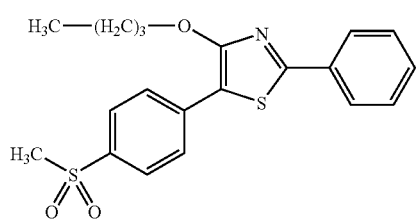
(3)
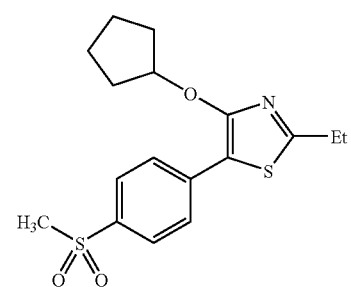
(4)
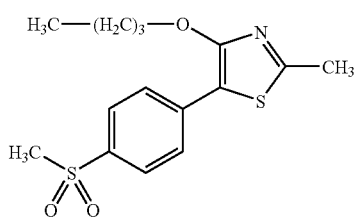
(5)
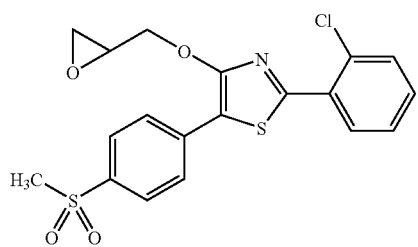
(6)
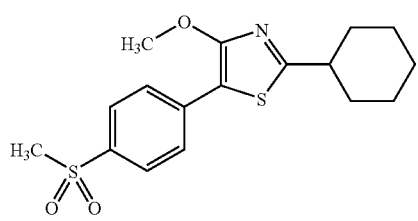
-continued
(7)
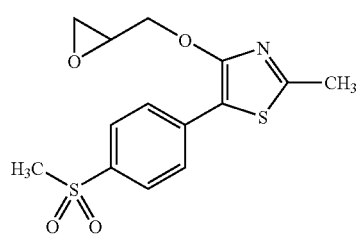
(8)
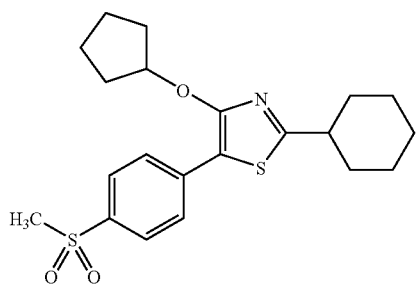
(9)
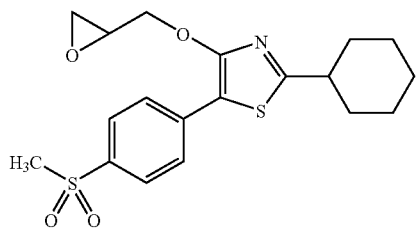
(10)
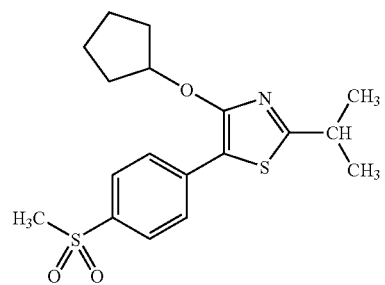
(11)
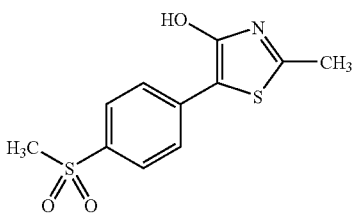
(12)
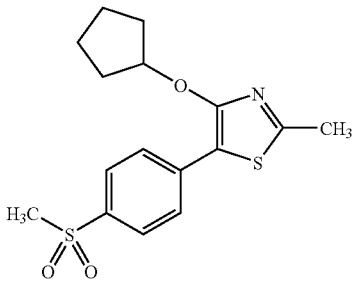

-continued

(13)
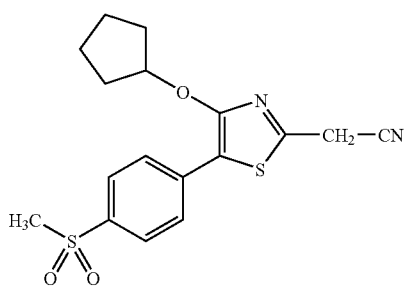

(14)
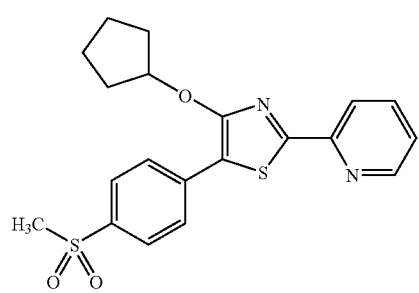

(15)
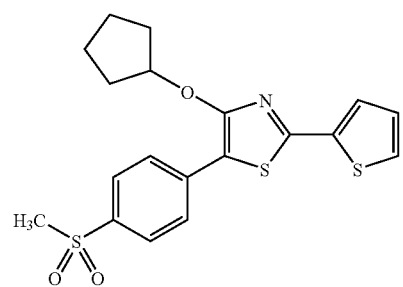

(16)
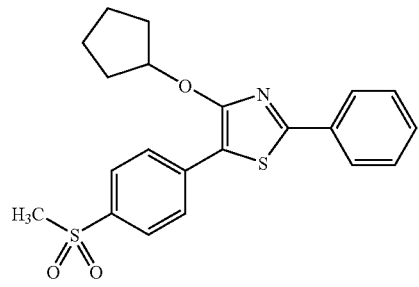

(17)
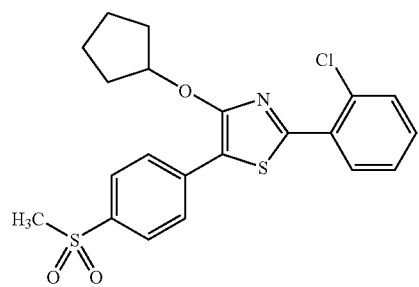

-continued

(18)
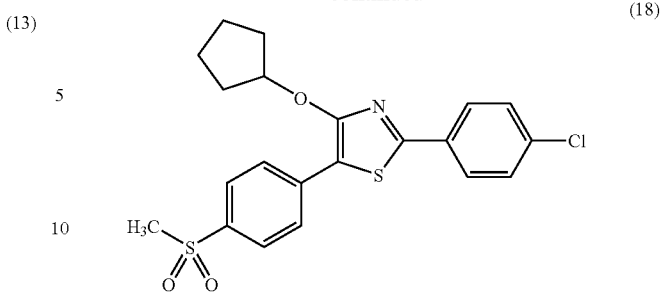

or a pharmaceutically acceptable salt, prodrug and/or solvate thereof.

The compounds of formula (I) can be obtained by available synthetic procedures. For example, they can be prepared by a process which is summarised in the following scheme:

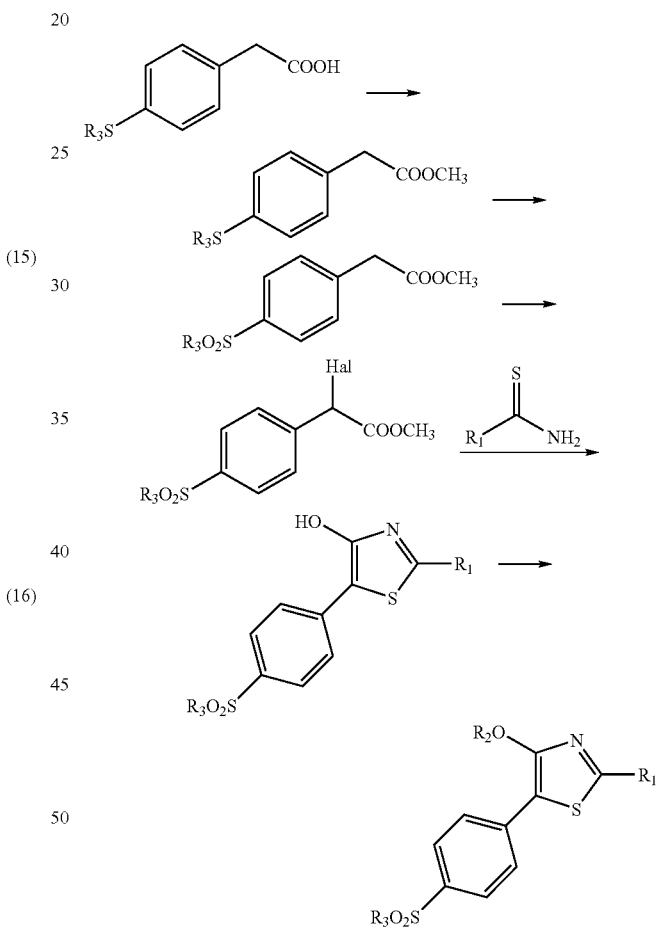

This process firstly comprises an esterification reaction of the compound 4-$R_3$-thiophenylacetic acid to render the methyl ester derivative. Said reaction can be carried out by using a methylating agent, such as MeI, in the presence of a salt, such as $NaHCO_3$, or by using MeOH as methylating agent in the presence of an acidic medium.

In the following step, the methyl ester derivative, optionally without any purification, is oxidized at the sulphur atom using an oxidizing agent, for instance, oxone, thus obtaining the sulfone compound from the thioether group.

Subsequent halogenation with an agent such as NBS, leads to the formation of the halide at the α-position of the ester group. The cycloaddition of this compound with different thioamides under heating yields $R_1$-substituted 5-(4-$R_3$-sulfonyl-phenyl)-thiazol-4-ol with a high degree of purity.

Thioamides used for the cycloaddition are obtained from the amides corresponding to Lawesson reagent as described in *J. Med. Chem* (34) 2158-2165, 1991 and *J. Org. Chem.* (65), 13, 3973, 2000. Said thioamides include compounds wherein $R_1$ is selected from hydrogen, substituted or unsubstituted $C_1$-$C_6$ alkyl, substituted or unsubstituted cycloalkyl, substituted or unsubstituted aryl and substituted or unsubstituted heterocyclyl as defined above.

The introduction of the $R_2$ radical through the hydroxyl group can be carried out by any method known by a skilled person to render the compound of formula (I) used in the present invention. In a particular embodiment, the hydroxyl group is reacted with an halide of formula $R_2$-Hal, preferably $R_2$—Br, to provide the compound of formula (I).

All reactants used in the mentioned reactions are commercially available.

The present invention further provides pharmaceutical compositions comprising the novel compound of formula (I) of the present invention, or pharmaceutically acceptable salts, solvates or prodrugs thereof and at least one pharmaceutically acceptable carrier, adjuvant and/or vehicle, for the administration to a patient.

In a particular embodiment, for its administration in the prevention and/or treatment of acute or chronic inflammatory diseases, the compounds of formula (I), their pharmaceutically acceptable salts, prodrugs and/or solvates will be formulated in a suitable pharmaceutical composition, in the therapeutically effective amount, together with one or more pharmaceutically acceptable carriers, adjuvants, and/or vehicles.

The term "carrier, adjuvant and/or vehicle" relates to molecular entities or substances with which the active ingredient is administered. Such pharmaceutical carriers, adjuvants or vehicles can be sterile liquids, such as waters and oils, including those of petroleum or with an animal, plant or synthetic origin, such as peanut oil, soybean oil, mineral oil, sesame oil and the like, excipients, disintegrants, wetting agents or diluents. Suitable pharmaceutical carriers are described in "Remington's Pharmaceutical Sciences" by E. W. Martin.

The pharmaceutical compositions can be administered by any suitable method of administration, for example, oral, parenteral (for example, subcutaneous, intraperitoneal, intravenous, intramuscular, etc.), rectal administration, etc., typically orally due to the chronic nature of the disease to be treated.

In a particular embodiment, said pharmaceutical compositions can be in an oral administration pharmaceutical form, either in solid or liquid form. Illustrative examples of oral administration pharmaceutical forms include tablets, capsules, granulates, solutions, suspensions, etc., and can contain conventional excipients such as binders, diluents, disintegrants, lubricating agents, wetting agents, etc., and can be prepared by conventional methods. The pharmaceutical compositions can also be adapted for their parenteral administration, in the form of, for example, sterile, lyophilized products, suspensions or solutions in the suitable dosage form; in this case, said pharmaceutical compositions will include suitable excipients, such as buffers, surfactants, etc. In any case, the excipients will be chosen according to the selected administration pharmaceutical form. A review of the different pharmaceutical forms for administering drugs and of their preparation can be found in "*Tratado de Farmacia Galénica*", by C. Faulí i Trillo, 10th Edition, 1993, Luzán 5, S. A. de Ediciones.

For its application in therapy, the compound of formula (I) will preferably be found in a pharmaceutically acceptable or substantially pure pharmaceutical form, i.e. the compound of formula (I) has a pharmaceutically acceptable purity level excluding pharmaceutically acceptable excipients and does not include material considered to be toxic at normal dosage levels. The purity levels for a compound of formula (I) are preferably greater than 50%, more preferably greater than 70%, more preferably greater than 90%. In a preferred embodiment, they are greater than 95%.

The therapeutically effective amount of the compound of formula (I) to be administered will generally depend, among other factors, on the individual to be treated, on the severity of the disease suffered by said individual, on the chosen method of administration, etc. For this reason, the doses mentioned in this invention must only be considered as guidelines for the person skilled in the art, and the latter must adjust the doses according to the aforementioned variables. Nevertheless, a compound of formula (I) can be administered once or more times a day, for example, 1, 2, 3 or 4 times a day, in a typical total daily amount comprised between 0.1 and 1000 mg/kg of body mass/day, preferably 10 mg/kg of body mass/day.

The compound of formula (I), its pharmaceutically acceptable salts, prodrugs and/or solvates, as well as the pharmaceutical compositions containing them can be used together with other additional drugs useful for treating acute and chronic inflammatory diseases. Said additional drugs can form part of the same pharmaceutical composition or alternatively, can be provided in the form of a separate composition for its simultaneous or non-simultaneous administration with the pharmaceutical composition comprising a compound of formula (I), or a pharmaceutically acceptable salt, prodrug or solvate thereof.

Another aspect of the present invention is a method for treating an acute or chronic inflammatory disease, which comprises administering to a patient who needs such treatment a therapeutically effective amount of a compound of formula (I) as defined above or a pharmaceutical composition thereof.

Within the scope of the present invention, the expression "acute and chronic inflammatory disease" relates to any disease, disorder or condition which results from the activation and pathogenic involvement of inflammatory/immune cells and inflammatory cytokine cascade under condition in which abnormal co-stimulation is a pathogenic mechanism. The predominant cells involved are inflammatory/immune cells such as monocytes, macrophages, APC, T, B and Natural Killer (NK) cells, plasma cells, granulocytes and mast cells, or combinations of the above cell subpopulations implicated in the diseases proposed for treatment.

The term "cytokine" refers to a secreted protein that affects the functions of other cells, particularly as it relates to the modulation of interactions between cells of the immune system or cells involved in the inflammatory response. Said cytokines are TNF-alpha (tumor necrosis factor-α), IFN-gamma (interferon-γ) and IL-8 (interleukin-8). IL-10 (interleukin-10) production is induced by high TNF-alpha levels and promotes a negative feed-back upon TNF-alpha production, upon blockade of pro-inflammatory cytokine transcription.

In a particular aspect of the invention, the acute or chronic inflammatory disease is selected from acute and chronic seropositive or seronegative olygoarthritis and polyarthritis, spondiloarthropathies, glomerulonephritis, colagenopathies, tubulo-interstitial nephritis, metabolic syndrome, atherosclerosis, osteoarthritis, asthma, chronic obstructive pulmonary disease, interstitial lung disease, multiple sclerosis, demyelinating diseases, meningitis, encephalitis, meningoencephalitis, inflammatory radiculopathies and peripheral neuropathies, inflammatory bowel disease, cirrhosis, hepatitis, heart failure, ischemic disease, renal failure, inflammatory cystitis, benign prostatic hyperplasia, prostatitis, myocarditis, pericarditis, uveitis, atopic dermatitis, eccema, urticaria, psoriasis, rosacea, allergic rhinitis, sepsis, septic shock, multiorganic failure, systemic autoimmune diseases such as systemic lupus erythematosus, vasculitis, dermatomyositis, amyloidosis or sarcoidosis, organ specific autoimmune diseases such as myasthenia gravis, thyroiditis or insulinitis, organ transplantation, infectious ant tumor induced inflammation, TNF-alpha dependent cellular degeneration, necrosis, apoptosis, graft versus host disease, cachexia and autocrine and paracrine pathological cell growth.

In a preferred embodiment, the acute or chronic inflammatory disease is seropositive or seronegative chronic polyarthritis, more preferably is rheumatoid arthritis.

The term "treatment" or "treat" in the context of this specification means the administration of a compound with a formulation according to the invention for preventing, alleviating or eliminating the disease or one or more symptoms associated to said disease. "Treatment" also includes preventing, alleviating or eliminating the physiological sequelae of the disease.

The term "alleviate" in the context of this invention is understood to mean any improvement of the situation of the treated patient—both subjectively (the feelings of or about the patient) and objectively (measured parameters).

Another aspect of the invention refers to the use of a compound of formula (I) as defined above as an imaging biomarker in imaging and pharmaco-imaging technologies, for finding immunological lesions, target cells and target molecules.

The pharmaco-imaging technology extends the scope of biomarkers obtained by the rapidly growing combination of adequate preclinical (molecular, cellular, organ and whole animal tracking and study of proof of concept and mechanisms, efficacy assessment, etc) and clinical (human medical) in vivo imaging technologies, to those valuable information data generated by compounds described herein and used as medicines.

The present invention is additionally explained below by means of examples. This explanation must by no means be interpreted as a limitation of the scope of the invention as it is defined in the claims.

EXAMPLES

Synthesis

Example 1

Synthesis of (4-methylthiophenyl)-acetic acid methyl ester

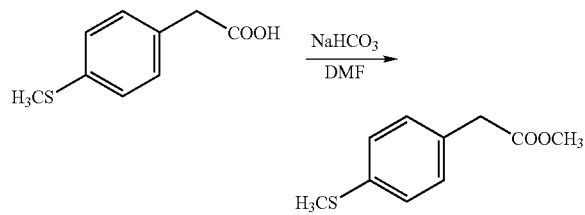

1.82 g (10 mmol) of the 4-methylthiophenylacetic acid were dissolved in 30 mL of DMF and 1.34 g (16 mmol) of $NaHCO_3$ are then added; the agitation mixture is stirred for 15 min approx. Next, 1.9 mL of $ICH_3$ are added while keeping agitation at room temperature for 24 h. Once this time elapsed the mixture is poured on water/ice. As no precipitation occurs ether is added and extracted. The organic phase is washed with water and after drying on sodium sulfate anhydride, the organic phase is concentrated in a rotary evaporator getting 1.92 g (9.7 mmol, 97% yield) of colorless oil which spectroscopic data confirm the expected structure. This product will be used in the next step of the synthesis process without purification as it provides a single stain in TLC (eluting dichloromethane/methanol 9/1).

RMN $^1H$ ($CDCl_3$): 7.2 (s, 4H) 3.7 (s, 3H) 3.5 (s, 2H) 2.4 (s, 3H $CH_3S$)

RMN $^{13}C$ ($CDCl_3$): 171.5 136.9 130.4 129.4 126.4 51.6 40.2 15.5

Example 2

Synthesis of (4-methylsulfonyl-phenyl)-acetic acid methyl ester

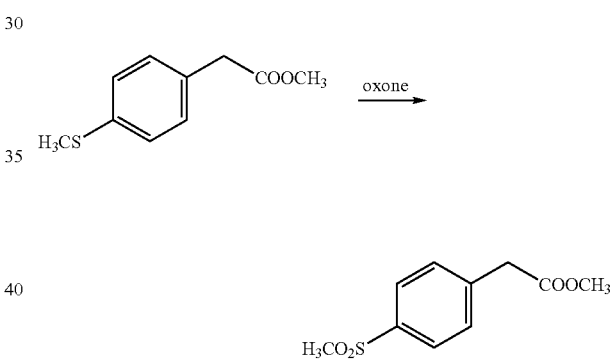

A solution of oxone 30.7 g (50 mmol) was added drop by drop in 80 mL of water to a solution of 3.4 g (17.3 mmol) of the compound obtained in example 1 in 100 mL of methanol keeping the reaction in a water/ice bath. Once added, agitation continues for 5 h, allowing temperature to get room level. Then, part of the solvent is concentrated at reduced pressure and the precipitated solid is filtered washing with water repeatedly. After drying, this solid weighs 3 g. Waters from filtering are extracted with dichloromethane, the organic phase is washed with water, dried on sodium sulfate anhydride and concentrated in a rotary evaporator obtaining 1 more g of product than expected, yield 4 g (17 mmol, 100% yield). This solid melts with decomposition at 57° C. and its purity is 99% by HPLC. Spectroscopic data confirm the expected structure:

RMN $^1H$ ($CDCl_3$): 7.9 (d, 2H), 7.5 (d, 2H), 3.7 (s,s 3+2H), 3.1 (s, 3H)

RMN $^{13}C$ ($CDCl_3$): 170.80 140.13 139 130.33 127.63 52.31 44.49 40.82

Example 3

Synthesis of bromo-(4-methylsulfonyl-phenyl)-acetic acid methyl ester

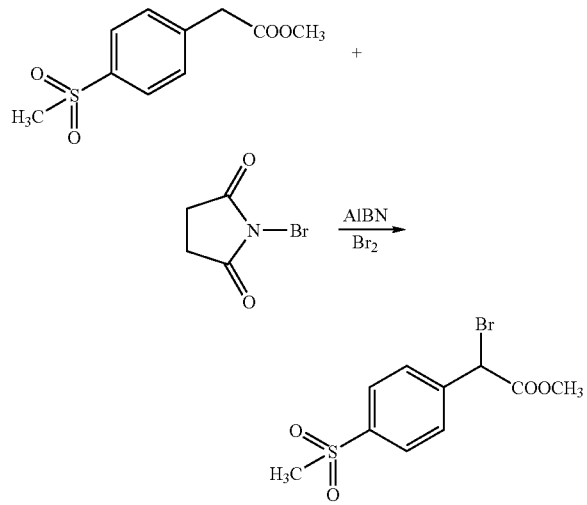

20 g (87.62 mmol) of the ester were dissolved in 300 mL of carbon tetrachloride; 19 g (105 mmol) of N-bromosuccinimide, 2 g (12.18 mmol) of azobisisobutyronitrile and 0.1 mL of bromine were added in portions. The reaction mixture was heated at 80° C. for 3 hours and, then cooled, filtered off and washed with dichloromethane. The filtrate was washed with water and then with brine. The solution was dried over anhydrous sodium sulfate and concentrated under vacuum to yield 28 g of an oil, which was purified by flash chromatography using heptane/ethyl acetate (1/1) as eluent. Concentration of the purer fractions yielded 19.63 g (72.94% of yield) of the bromoderivative compound.

mp: 81.8-83.3° C.

NMR $^1$H (CDCl$_3$), δ: 7.9 (d, 2H), 7.75 (d, 2H), 5.4 (s, 1H), 3.8 (s, 3H), 3.1 (s, 3H).

NMR $^{13}$C(CDCl$_3$), δ: 168.0 (C); 141.6 (C); 141.1 (C); 129.8 (CH); 127.8 (CH); 53.7 (CH); 44.7 (CH$_3$) and 44.2 (CH$_3$) ppm.

Example 4

Synthesis of 2-methyl-5-(4-methylsulfonyl-phenyl)-thiazol-4-ol

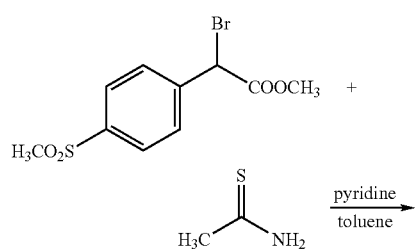

16.7 g (54.3 mmol) of the ester obtained in example 3 were dissolved in 400 mL of toluene, 19 mL of pyridine and 4.08 g (54.34 mmol) of the thioamide were then added. The reaction mixture is heated at 80° C. (bath temperature) with agitation for 2 h. Next, the mixture was left to cool and the precipitate solid was filtered, washed with water (2×50 mL) and then with ether (2×30 mL). The product was dried under vacuum to yield 7 g (26 mmol, 47.86% yield) of a cream solid melting at 216-226° C.

Spectroscopic data confirm the structure of the expected product.

RMN $^1$H (d$^6$DMSO) δ: 11.8 (s, 1H) 7.8 (m, 4H) 3.1 (s, 3H) 2.6 (s, 3H) ppm

RMN $^{13}$C (d$^6$DMSO): 162.9 (C); 159.4 (C); 146.2 (C); 143.0 (C); 128.0 (CH); 126.1 (CH); 104.4 (C); 44.2 (CH$_3$); 19.9 (CH$_3$) ppm.

Example 5

Synthesis of 4-cyclopentyloxy-5-(4-methylsulfonyl-phenyl)-2-methyl-thiazole

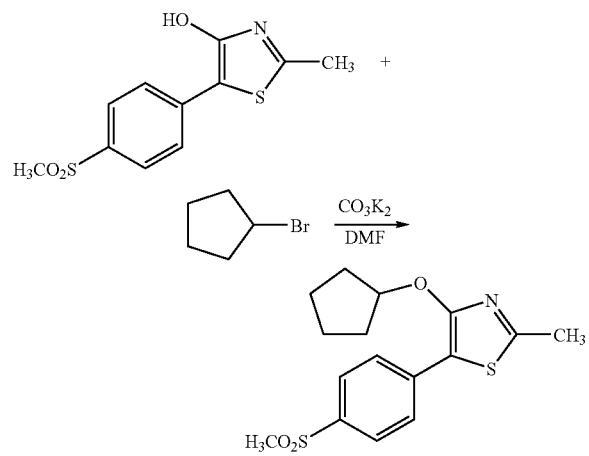

7.0 g (26 mmol) of the hydroxythiazole obtained in example 4 and 8.8 g (63.67 mmol) of potassium carbonate were dissolved in 200 mL of DMF. Cyclopentylbromide, 14 mL (130 mmol), were added dropwise. The reaction mixture was heated at 80° C. for 3 hours and then cooled, poured over a mixture of ice/water and extracted with ethyl acetate. The organic phase was washed with water (3×100 mL), dried over anhydrous sodium sulfate and concentrated to give 12 g of a crude material which crystallized from heptane/ether (1/1). Purification of the product by flash chromatography using heptane/ethyl acetate (2/1) as eluent yielded 6.7 g (19.85 mmol, 76.39% of yield) of compound 12.

mp: 124.6-125.2° C.

NMR $^1$H (CDCl$_3$), δ: 7.9 (dd, 4H), 5.4, (m, 1H), 3.0, (s, 3H), 2.6, (s, 3H), 1.7-2.0 (m, 8H) ppm NMR $^{13}C(CDCl_3)$, δ: 162.6 (C); 159.5 (C); 138.3 (C); 137.1 (C); 128.1 (CH); 126.8 (CH); 109.1 (C); 83.7 (CH); 45.0 (CH3); 33.5 ($CH_2$); 24.1 ($CH_2$); 20.4 ($CH_3$) ppm Biological Assays Material and Methods 1. Subjects The study was performed on heparinized peripheral blood obtained by venopunction from healthy volunteers and from patients with rheumatoid arthritis.

Healthy volunteers were blood-donors under routine control within the hospital practice.

Patients with rheumatoid arthritis included in this study complied with the diagnosis criteria of the American College of Rheumatology and exhibited a clinically active disease by the time of the inclusion visit having been treated for at least 6 months with 20 mg/week oral Methrotexate. The degree of disease activity was defined as follows: a) DAS28≧3.2 and/or b) 6 or more swollen articulations and 6 or more painful articulations. As exclusion criteria were considered the following: a) to suffer from active infectious diseases in the inclusion visit; b) to suffer from oncological diseases prior the inclusion; 3) to suffer from another systemic or organ specific auto-immune disease which had not entered into a complete remission at least one year prior the inclusion visit; d) to suffer from a severe renal, cardiac or hepatic condition not related with the changes at those levels induced by the rheumatoid arthritis as main disease; e) to suffer a severe deterioration of the general status due to a condition not related with the main disease; f) to have received treatment with corticosteroids, immunosuppresors, cytostatic or any other drugs with known activity on the immune system during the year prior the inclusion visit with the exception of the indicated doses of Methrotexate; 7) to be pregnant or within the puerperium in the inclusion visit.

The study was approved by the Investigational Committee of the AlcaláUniversity, Madrid, Spain.

2. Materials

Tissue culture plates, 96 wells flat bottom with low evaporation lid, 353073 Falcon, Becton Dickinson Labware, Franlklin Lakes, 07417-1886, NJ, USA).
Non sterile plates, 96 wells V bottom (Greiner, Soria Greiner, Madrid, España).
Disposable Pipettes Pasteur (Brand, Alemania).
Adjustable volume Pipettes Pipetman P de 20, 200, 1000 and 5000 µl (Gilson, Francia).
Eppendorf multipipette 4780 (Hamburg, Germany).
Sterile tips Eppendorf (Hamburg, Germany).
Virgin propilen sterile tips (Daslab, Madrid, Spain).
Sterile plastic tubes 5 and 10 ml (Daslab, Madrid, Spain).
Sterile centrifuge tubes 15 and 50 ml (BD Falcon, Franklin Lakes, USA).
Cytometer polyestirene tubes 5 ml (BD Falcon, Franklin Lakes, USA).
Blood extraction tubes with heparin 10 ml (Venojet, Terumo Europe, Belgium)
Plasma extraction tubes 10 ml (BD Vacutainer, Plymouth, UK)
Pipet filler, Pipetboy plus (Flow Lab., Germany).
Sterile filtres 22 µm Millex-GS (Millipore, Molshein, France).
Crystal slide covers (Hirschman, Germany).
Count chamber Neubauer (Saaringia, Germany).
Vertical laminar flux chamber Herasafe HS12 (Heraeus, Germany).
Cell culture stove with $CO_2$ regulation Heracell 150 (Heraeus, Germany)).
Refrigerated centrifuge Beckman. Multifuge 3SR (Heraeus, Germany).
Freezer −70° C. (Selecta, Tarrasa, Spain).
Mycroscope Olympus CHS-2 (Olympus, Tokyo, Japan).
Flow Cytometer FACScalibur (Becton Dickinson, Mountain View USA), with software and analyser BD Cellquest Pro v. 5.5.1.
BD FACS Arrray Bioanalyser.
Enzyme-immunoanalysis reader (Titertek Multiscan Plus, Flow laboratories).
Radioactivity beta counter Beckman 3. Reagents Used in the Separation and Identification of Cell Subsets Simple Chloride Saline (SSF) Apiroserum (Ibys, Madrid, Spain).
Lymphoprep (Ficoll-Hypaque, Nyegaard Co, Oslo, Norway).
Blue Trypan (Flucke A G., Buchs S G., Germany).
PBS FACS FLOW (Becton Dickinson).
HEPES buffer (Reactivos de Sigma y Panreac)
Methyl-$^3$H tymydine ($^3$[H]-T). Specific activity 60 Ci/mmol (American Radiochemicals, ITISA, Madrid, Spain).
Monoclonal antibodies used in the immunofluorescence and flux cytometry studies: Table 1

TABLE 1

Monoclonal antibodies used in the study:

| CD* | Ac Mo | Cell subset | Subclass | Fluorochrome |
| --- | --- | --- | --- | --- |
| 62L | SK11 | Leucocytes. L-Selectin | IgG2a | Phycoerythrine (PE) |

*Defined in the "7th Workshop on Human Leucocyte Differentiation Antigens".

4. Reagents Used in the Cell Cultures

Complete Medium made of RPMI-1640 (Cambrex Bio-Sciences B4800 Verviers, Belgium) supplemented with 1% L-Glutamine 200 mM y 25 mM Hepes (Flow Lab., Irvine, Calif., USA).
Phoetal bovine serum (FCS) (Gibco, Grand Island, N.Y., USA).
Culture medium: complete medium was used by adding 10% FCS. Complement was eliminated from all serum by heating to 57° C. during 45 minutes.
Phytohaemaglutinin M (PHA) (Sigma Ref #L-8902, Lot#115K4132, Sigma, Madrid, Spain).
LPS (*E. coli* 0111: B4 strain, Invivo gene, San Diego Calif. 92121, USA).
Antibiotic mixture. A mixture of Sodium Ampycilline 10 mg/ml (Britapen, Beecham A., Toledo, Spain), Gentamycin sulphate 1.6 mg/ml (Tamadit Lab., Dr. Esteve S A., Madrid, Spain) and Amphotherycine B 0.5 µg/ml (Fungizona, Squibb, Esplugues, Barcelona, Spain) was added to the culture medium.
Anti-CD3 monoclonal antibody (Orthoclone OKT3, Orthopharmaceutical Corporation, Raritan, N.J., USA).
Anti-CD28 monoclonal antibody (Cion 15E8, Menarini, Madrid, Spain).

5. Obtention of Biological Samples a) Venous blood: Mononuclear cells were obtained from venous blood as collected by antecubital venous punction. Fifty ml of blood were extracted and stored in lithium heparin tubes (Venojet), further diluted with saline 1/1 (vol/vol) being all performed under sterile conditions.

b) Human Cell subsets harvesting. For isolating PBMC, the remaining blood components were separated by a density gradient on Ficoll. This method is based on the differences on density of blood cells. In a 50 ml centrifuge tube containing the diluted and heparinized blood, 15 ml Ficoll-Hipaque (density 1.077 g/ml) was carefully placed on. After 45 minutes centrifugation (400×g), three strati were obtained (erythrocytes, Ficoll and plasma), separated by two interfaces: PBMC are contained in the one located between the diluted plasma and the Ficoll. It can be collected by aspirating with a Pasteur pipette. Cells so obtained are re-suspended in SSF and centrifuged (300×g during 10 minutes); supernatant is thrown out (washing out process) and the cellular pellet is re-suspended in RPMI 1640 medium with 10% of PBS.

6. Count and Viability Study

In an cell suspensions the cell concentration and viabilities were determined with a 0.1% dilution of Blue Trypan and Neubauer chamber mycroscope counting. The percentage of living cells was established by the ability of dyeing exclusion. The experiment only continued when the cell viability was above 95%.

7. Serum Cytokines Quantification by ELISA

In order to quantify the serum cytokines concentration, the extracted blood was stored in tubes both with and without anti-coagulant (collected by antecubital venopunction and arterial catheter, respectively). Blood was allowed to coagulate at room temperature in the laboratory, further separating the serum by centrifugation (600×g during 20 minutes). Supernatant were collected, filtered, divided in aliquotes and stored at −70° C. Concentration assays for different cytokines were performed by using the commercial kits described in Table 2.

TABLE 2

Commercial ELISA kits used in this study

| Cytokine | Quantification sensibility supernatants (pg/ml) | PM in (KDa) | Company |
| --- | --- | --- | --- |
| TNF-alpha | 3.83 pg/ml | 17 | Bender |

Supernatants were unfrozen up to the room temperature and faced against the respective anti-cytokine by fixing them in the plate bottom and incubating them during a variable time. Subsequently, wash-outs were carried out and the substances recommended by the corresponding company were added in order to allow a colorimetric reaction, in a proportional manner to the amount of cytokine present in the supernatant. The results were assessed with the enzymo-immunoanalysis reader Multititer Plus (Tiertek Multiscan Plus, Flow Laboratories). These results were compared with a standard curve obtained from known concentrations of each cytokine as provided by the company.

The analysis of the standard curves and subsequent interpolation was performed with the software Delta Soft II version 4.1 (Biometallics, Inc.) in an Apple Macintosh computer. Cytokine concentrations were converted to molar in order to calculate the molecular ratios of each case and the number of soluble molecules.

8. Immuno-Phenotype Assays

Direct immuno-fluorescence techniques of one colour with monoclonal antibodies phycoerythrin-labeled (PE) was used. PE is a fluorescent substance excitable with a 488 nm laser, which emits at 570 nm, and it is detectable and easily distinguishable by a flow cytometer. By using the antibody described in Table 1, a direct labelling was performed: PBMC labelling: the process consisted in a labelling using 96 well V bottom plates. In each well, $5\times10^4$ cells are located, and afterwards centrifugated at 400×g during 5 minutes. After washing-out, cells are re-suspended and 5 μl of the corresponding monoclonal antibody are added. Cells are again re-suspended and the plate is incubated in darkness, during 20 minutes, at 4° C. Subsequently, 150 μl PBS are added and two wash-outs are performed. Finally, it is re-suspended in 150 μl PBS and collected in a cytometer tube, adding PBS up to a final volume of 0.3 ml.

For the counting, a FACSCalibur flow cytometer equipped with argon laser tuned at 488 nm was used in order to induce phycoerythrin fluorescence. The equipment, apart from the fluorescence channels, also provided information about the size (FSC) and cellular complexity (SSC).

As negative controls, the study cells with no labelling and other irrelevant labelled with monoclonal antibodies of equal isotypes than the ones used in the study (IgG1-FITC, PE y TC, IgG2a FITC, PE, TC), were used.

9. Cellular Cultures and Functional Studies

General conditions of the culture: all cellular cultures were performed under sterile conditions within a vertical laminar flux chamber, using either sterile disposable materials or sterilized by ethylene oxide or sterilizer apparatus. Cultures were kept in a stove at 37° C. under 5% $CO_2$ and 95% relative humidity.

10. Proliferation study with $^3[H]$-Thymidine

Faced against a mitogen stimulation, lymphocytes suffer a blastogenesis and cellular differentiation process. The method used to quantify the cellular proliferation was the assay of the incorporation of $^3[H]$-Thymidine to the DNA de novo synthesized, and the emission of betha-radiation from the cellular cultures dried extracts (to which the tritiated base was added) was detected before its ending and harvesting. In the different experiments performed to study the proliferation, the purified cellular preparations were incubated in 96 microwells plain bottom plates at concentrations of $5\times10^4$ cells/well (200 μl final volume), in the presence of different concentrations of various mitogens with triplicate repetitions and along 4 days of culture.

The response to a specific stimuli depended on the density and cell type studied, as well as of the culture time and of the mitogenic agent concentration.

Twenty to twenty four hours before finishing the cellular culture, 1 microCi $^3[H]$-Thymidine was added to each well; cultures were harvested by aspiration through a glass filter by using a specific culture harvester.

DNA synthesis was expressed in counts per minute (c.p.m.). Each assay was performed in triplicate, rejecting those data with a variability higher than 10% in the mean of the triplicate as they might indicate a technical error or a contamination of the culture. Cultures were performed with a constant amount of cells per well as well as with a constant volume of 200 μl. All mitogens and cytokines were first tested by carrying out dose-response curves and time-response.

11. Assays for Analytical Determination by Quantitative Multiparametric Flow Citometry (BD™ Cytometric Bead Array o CBA)

CBA protocol was followed according to the manufacturer's instructions. The election of microparticles was performed following the summary of FIG. 1. Those which showed a little risk of spectral overlapping were finally selected.

The catalogue number and batch of each reagent used for this experimental development is shown in Tables 3 and 4. The acquisition on samples was performed with the BD FACS Array Bioanalyser System (FACSArray, Becton Dickinson, San Jose, Calif., USA) and the analysis of the results was completed with the software FCAP Array (Becton Dickinson) in a PC computer.

Briefly, the experimental protocol consisted of a plate prewashing out with Wash Buffer. After decantation, the mixture of capture microparticles was re-suspended in the vortex. Standards and samples were added in the adequate dilution. After permanent stirring incubation during 1 h, the PE detection reagent was added and incubated again during 2 h at room temperature. After a washing-out, the acquisition was performed in the flow cytometer.

TABLE 3

Kit CBA Human Soluble Protein Multiplex Flex Set System.

| Reagent | N° catalogue | Batch | Sensitivity |
|---|---|---|---|
| Master buffer kit 500 test | 558265 | 95098 | |
| Assay Diluent | 51-90003992 | 86192 | |
| Capture Bead Diluent | 51-90003804 | 90262 | |
| Detection Reagent Diluent | 51-90003993 | 95811 | |
| Wash Buffer | 51-90003798 | 85964 | |
| Instrument Setup Bead A1 | 51-90003855 | 87987 | |
| Instrument Setup Bead A9 | 51-90003858 | 95933 | |
| Instrument Setup Bead F1 | 51-90003851 | 89231 | |
| Instrument Setup Bead F9 | 51-90003854 | 94229 | |
| PE Instrument Setup Bead F1 | 51-9005038 | 94498 | |
| PE Positive Control Detector | 51-9005065 | 92154 | |
| CBA Flex Set Kits | | | |
| IL-1betha (B4) | 558279 | 99164 | 2.3 pg/ml |
| IL-8 (A9) | 558277 | 85109 | 1.2 pg/ml |
| IL-10 (B7) | 558274 | 97196 | 0.13 pg/ml |
| TNF-α (D9) | 558273 | 85106 | 0.7 pg/ml |
| IFN-γ (E7) | 558269 | 81562 | 1.8 pg/ml |

TABLE 4

Batches of reagents included in the design of the Kit CBA Flex Set.

| Reagent | Standard | Capture microparticles | Fluorescent reagent (PE) |
|---|---|---|---|
| IL-1betha (B4) | 94205 | 98173 | 98174 |
| IL-8 (A9) | 84854 | 87670 | 77948 |
| IL-10 (B7) | 70333 | 96280 | 95934 |
| TNF-α (D9) | 65908 | 87667 | 77294 |
| IFN-γ (E7) | 80390 | 87664 | 77136 |

Statistical Analysis

Results of the experimental tests were presented as means and standard and estimate errors of the mean, according to the type of distribution.

For the statistical analysis, the nature of the distributions was firstly analysed by using the contrast of normality of Shapiro-Whilk. The non-parametric contrast of Mann-Whitney U was used to establish comparisons. In all cases, lower than 5% signification levels were valued ($p<0.05$).

The statistical analysis was performed with the software SPSS 11.0 (SPSS Inc. Headquarters, 233 S. Wacker Drive, 11th floor. Chicago, Ill. 60606)

Results of the Studies on the Immune Modulator Effects of Compound 12

Immune Modulator Effects of Compound 12 on the Production of TNF-Alpha, IFN-Gamma and Other Cytokines by the Peripheral Blood Mononuclear Cells (PBMC) on Healthy Volunteers and Patients with Rheumatoid Arthritis.

Example 6

Effects of Compound 12 on TNF-Alpha Production

Effects of compound 12 on TNF-alpha production by PBMC of healthy volunteers in the presence or in the absence of LPS were first investigated. PBMC ($5\times10^4$ cells/well, 200 μl) from 10 healthy volunteers were cultured in parallel in duplicate in tissue culture plates, 96 well, flat-bottom with low evaporation lid (353072 Falcon, Becton Dickinson labware, Franklin Lakes, USA, 07417-1886 NJ) in complete medium (RPMI-1640 with glutamine Cat BE-12-70F, Cambrex Biosciences, B4880 Verviers, Belgium), supplemented with phoetal bovine serum (origin USA, Gibco ref. 26140-079) and a solvent concentration of $10^{-6}$ M alone or supplemented with $10^{-6}$ M or $10^{-7}$ M of compound 12, in the presence and in the absence of LPS (10 microg/ml; E. coli LPS 0111:B4 strain in-vivo gene, San Diego Calif. 92121 USA) during 24 hours. Supernatant of cultures were frozen at −20° C. and the concentration of TNF-alpha was quantified with ELISA species-specific (enzyme-linked immunosorbent assay for quantitative detection of tumour necrosis factor-alpha: human TNF-alpha ELISA BM S223/4TEUCE, Bender Med System Inc, Burlinghane Calif. 94010).

Figure 2:
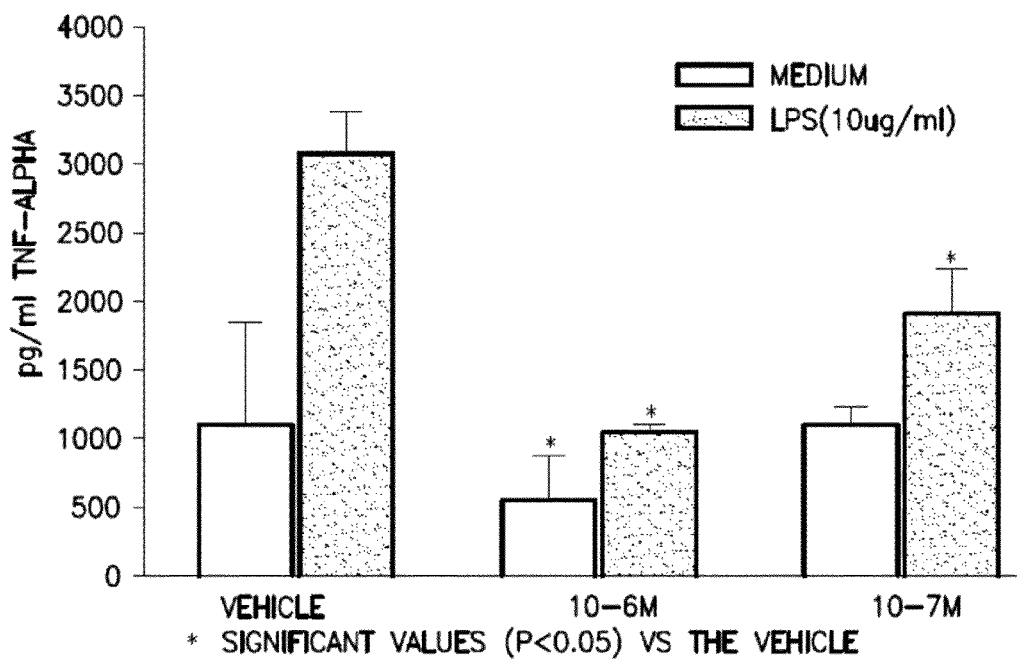
FIG. 2: Influence on TNF-alpha production in LPS-stimulated PBMC from healthy volunteers (n=10) by compound 12. Columns represent the median and standard error of the duplicate cultures performed in each sample in the different experimental conditions. Asterisks represent statistically significant differences ($p<0.05$) of the corresponding data with respect to the vehicle for each experimental condition.

FIG. 2 shows that the presence of compound 12 in the culture, at concentrations of $10^{-6}$ M and $10^{-7}$ M diminished in a statistically significant manner the TNF-alpha concentration as quantified in the supernatant of the culture of LPS-stimulated PBMC ($p<0.05$). Moreover, compound 12, at $10^{-6}$ M also lowered the spontaneous TNF-alpha production by PBMC.

TABLE 5

TNF-alpha production by healthy volunteers. Results are indicated as median ± standard error values of the secreted cytokine. Statistically significant results are indicated in bold, with their corresponding p values (data with respect to the vehicle for each experimental condition) included in parenthesis.

| | TNF-alpha production in PMBC from healthy volunteers (pg/mL) | | |
|---|---|---|---|
| n = 10 | vehicle | $10^{-6}$ M | $10^{-7}$ M |
| medium | 1118.00 ± 800.00 | 551.60 ± 324.17 (0.009) | 1121.00 ± 100.48 (0.114) |
| LPS (10 μg/ml) | 3084.63 ± 450.00 | 1064.91 ± 52.82 (0.005) | 1938.00 ± 487.74 (0.028) |

Immune modulator effects of compound 12 were further characterised on the production of a cytokine pannel by PBMC either after monocyte stimulation with either LPS or lymphocyte activation with a combination of monoclonal antibodies anti-CD3 and anti-CD28. This study was performed in the presence or absence of titulated doses of compound 12 in cultures of PBMC obtained from healthy volunteers and patients with rheumatoid arthritis.

PBMC ($5\times10^4$ cells/well) from 13 healthy volunteers were cultured in duplicate in 200 μl of complete medium supplemented with the highest solvent concentration ($10^{-6}$ M), or $10^{-6}$ M and $10^{-7}$ M compound 12 and in the presence and in the absence of LPS (10 μg/ml) during 24 hours. Supernatant of cultures were frozen at −20° C. and quantification was carried out by BD FACS Array Bioanayliser (BD Biosciences Cat No. 340128, San Diego Calif. 92121) by using specific reagents for the simultaneous assay of the indicated cytokines concentration (CBA Flex Multiplex Set (BD™ Cytometric Bead Array, CBA: IL-1-betha, IL-8, IL-10, TNF-alpha and IFN-gamma Becton Dickinson Biosciences Pharmingen, San Diego Calif. 92121).

Figure 3:
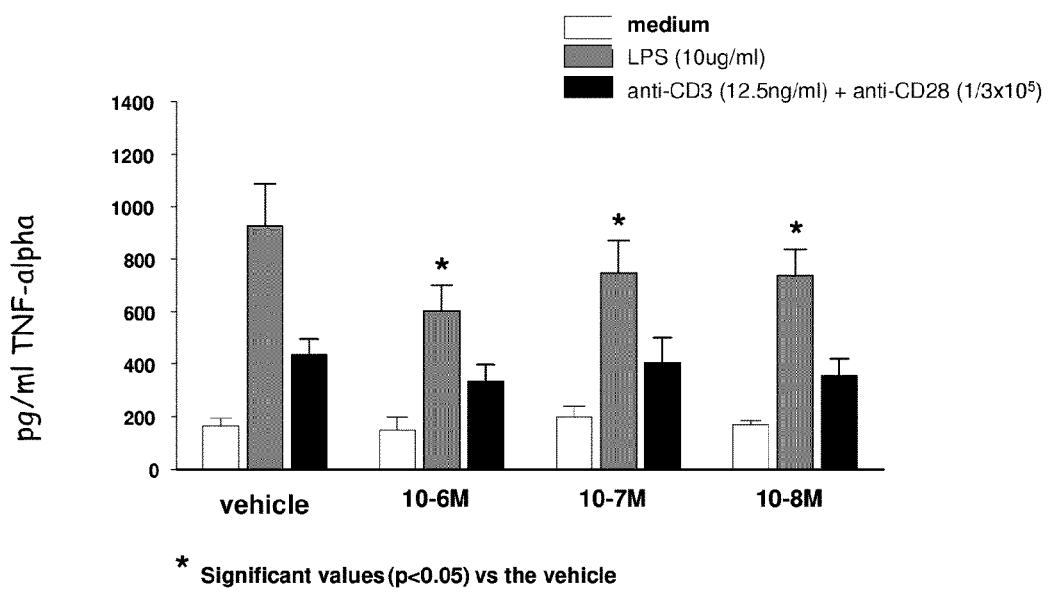
FIG. 3: Influence on TNF-alpha production in LPS- or TCR/CD3+CD28-stimulated PBMC from healthy volunteers (n=10) by compound 12. Columns represent the mean and standard error of the duplicate cultures performed in the samples in the different experimental conditions. Asterisks represent statistically significant differences ($p<0.05$) of the corresponding data with respect to the vehicle for each of the different experimental conditions.

The presence of compound 12 in the culture, at concentrations $10^{-6}$ M, $10^{-7}$ M and $10^{-8}$ M diminished TNF-alpha production by the PBMC of healthy volunteers stimulated with LPS in a statistically significant manner ($p<0.05$) (FIG. 3). On the contrary, neither TNF-alpha secretion by PBMC stimulated with monoclonal antibodies anti-CD3 and anti-CD28 nor spontaneous one (as observed in the absence of exogenous stimuli) was modified by compound 12.

TABLE 6

TNF-alpha production by healthy volunteers. Results are indicated as mean ± standard error values of the secreted cytokine. Statistically significant results are indicated in bold, with their corresponding p values (data with respect to the vehicle for each experimental condition) included in parenthesis.

| | TNF-alpha production in PMBC from healthy volunteers (pg/mL) | | | |
|---|---|---|---|---|
| n = 13 | vehicle | $10^{-6}$ M | $10^{-7}$ M | $10^{-8}$ M |
| medium | 163.84 ± 30.00 | 148.31 ± 50.00 (0.422) | 197.81 ± 40.00 (0.249) | 168.49 ± 16.00 (0.65) |
| LPS (10 µg/ml) | 923.93 ± 160.00 | 602.12 ± 100.00 (0.002) | 746.84 ± 125.00 (0.046) | 738.81 ± 100.00 (0.055) |
| anti-CD3 (12.5 ng/ml) + anti-CD28 (⅓ × $10^5$) | 435.81 ± 60.00 | 34.21 ± 63.00 (0.116) | 404.11 ± 97.00 (0.753) | 355.62 ± 65.00 (0.422) |

In another experiment, PBMC (5×10⁴ cells per well) from 7 patients with rheumatoid arthritis were cultured in duplicate in 200 µl of complete medium supplemented with the highest solvent ($10^{-6}$ M), and $10^{-6}$ M, $10^{-7}$ M and $10^{-8}$ M compound 12 and in the presence and absence of either LPS (10 µg/ml), or anti-CD3 (12.5 ng/ml) (Orthoclone OKT3, Orthopharmaceutical Corporation, Raritan N.J., USA)+anti-CD28 (⅓× $10^5$) (Clon 15E8, Menarini, Madrid, Spain), during 24 hours. Culture supernatants were frozen at −20° C. and the concentration of TNF-alpha quantified by BD FACS Array Bioanalyser by using CBA Flex Set (Becton Dickinson), specific for determining the concentration of that cytokine, following the manufacturer instructions.

Figure 4:
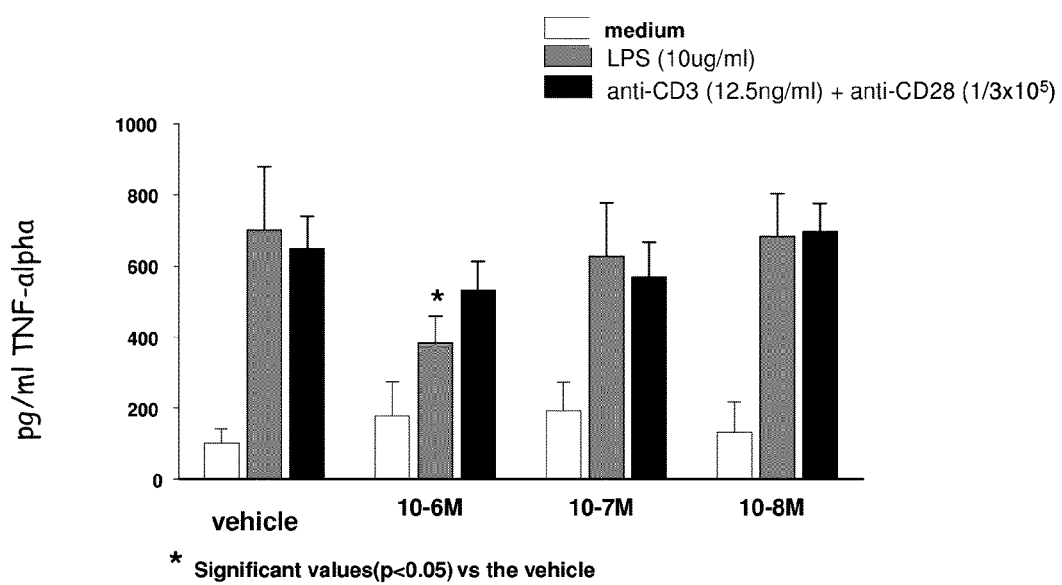
FIG. 4: Influence on TNF-alpha production in PBMC from patients with rheumatoid arthritis by compound 12. Columns represent the mean and standard error of the duplicate cultures performed in each sample in the different experimental conditions. Asterisks represent statistically significant differences ($p<0.05$) of the corresponding data with respect to the vehicle for each different experimental condition.

In LPS-stimulated PBMC from patients with rheumatoid arthritis, the production of TNF-alpha was significantly inhibited by compound 12 at a concentration of $10^{-6}$ M (p<0.05) (FIG. 4). The presence of compound 12 in the culture neither inhibited the spontaneous TNF-alpha production nor the one obtained after stimulation with monoclonal antibodies anti-CD3 and anti-CD28 in PBMC from patients with rheumatoid arthritis.

Example 7

Effects of Compound 12 on the Production of IFN-Gamma

PBMC (5×10⁴ cells per well) from 13 healthy volunteers were cultured in duplicate in 200 µl of complete medium supplemented with the highest solvent concentration ($10^{-6}$ M), and $10^{-6}$ M, $10^{-7}$ M and $10^{-8}$ M of compound 12 in the presence or absence, either of LPS (10 µg/ml), or anti-CD3 (12.5 ng/ml)+anti-CD28 (⅓×$10^5$), during 24 hours. Culture supernatants were frozen at −20° C. and the concentration of IFN-gamma was quantified by BD FACS Array Bioanalyser by using CBA Flex Set (Becton Dickinson), specific to determine the concentration of IFN-gamma, following the manufacturer instructions.

Compound 12, at a concentration of $10^{-6}$ M significantly inhibited the production of IFN-gamma by PBMC from healthy volunteers either LPS-stimulated or stimulated with monoclonal antibodies anti-CD3 and anti-CD28 (p<0.05) (FIG. 5).

TABLE 7

TNF-alpha production by patients with rheumatoid arthritis. Results are indicated as mean ± standard error values of the secreted cytokine. Statistically significant results are indicated in bold, with their corresponding p values (data with respect to the vehicle for each experimental condition) included in parenthesis.

| | TNF-alpha production in PMBC from patients with rheumatoid arthritis (pg/ml) | | | |
|---|---|---|---|---|
| n = 8 | vehicle | $10^{-6}$ M | $10^{-7}$ M | $10^{-8}$ M |
| medium | 100.64 ± 40.00 | 177.32 ± 95.00 (0.735) | 191.33 ± 80.00 (0.735) | 131.95 ± 85.00 (0.735) |
| LPS (10 µg/ml) | 700.39 ± 180.00 | 383.75 ± 75.00 (0.05) | 626.57 ± 150.00 (0.237) | 683.40 ± 120.00 (0.499) |
| anti-CD3 (12.5 ng/ml) + anti-CD28 (⅓ × $10^5$) | 648.72 ± 90.00 | 532.07 ± 80.00 (0.31) | 568.47 ± 97.00 (0.612) | 695.81 ± 79.00 (0.398) |

TABLE 8

IFN-gamma production by healthy volunteers. Results are indicated as mean ± standard error values of the secreted cytokine. Statistically significant results are indicated in bold, with their corresponding p values (data with respect to the vehicle for each experimental condition) included in parenthesis.

| | IFN-gamma production in PMBC from healthy volunteers (pg/mL) | | | |
|---|---|---|---|---|
| n = 13 | vehicle | $10^{-6}$ M | $10^{-7}$ M | $10^{-8}$ M |
| medium | 283.78 ± 90.00 | 189.72 ± 40.00 (0.279) | 296.28 ± 90.00 (0.807) | 279.16 ± 60.00 (0.807) |
| LPS (10 µg/ml) | 860.42 ± 105.00 | 649.61 ± 120.00 (0.011) | 919.53 ± 130.00 (0.552) | 1049.85 ± 230.00 (0.382) |
| anti-CD3 (12.5 ng/ml) + anti-CD28 (⅓ × $10^5$) | 11802.22 ± 1300.00 | 7927.17 ± 1003.00 (0.019) | 11552.08 ± 1600.00 (0.917) | 10254.66 ± 1500.00 (0.196) |

The spontaneous secretion of IFN-gamma by PBMC from healthy volunteers was not modified by compound 12.

PBMC (5×$10^4$ cells/well) from 7 patients with rheumatoid arthritis were cultured in duplicate 200 µl of complete medium supplement with the highest solvent concentration ($10^{-6}$ M), and $10^{-6}$ M, $10^{-7}$ M and $10^{-8}$ M of compound 12, in the presence and absence either of LPS (10 µg/ml), or anti-CD3 (12.5 ng/ml)+anti-CD28 (⅓×$10^5$), during 24 hours. Culture supernatants were frozen at −20° C. and IFN-gamma concentration was assessed by BD FACS Array Bioanalyser by using CBA Flex Set, specific to determine IFN-gamma concentration, following the manufacturer instructions.

The presence of compound 12, at concentrations of $10^{-6}$ M, $10^{-7}$ M and $10^{-8}$ M, significantly lowered the production of IFN-gamma by PBMC from patients with rheumatoid arthritis when induced by the stimulation with monoclonal antibodies anti-CD3 and anti-CD28 (p<0.05) (FIG. 6). Compound 12 modified neither the spontaneous IFN-gamma secretion nor the LPS-induced by the PBMC from healthy volunteers.

Example 8

Effects of Compound 12 on Interleukin 8 (IL-8) Production

The effect of compound 12 on the IL-8 production by the PBMC from healthy volunteers was further investigated, both in the presence and absence of LPS stimuli and monoclonal antibodies anti-CD3 and anti-CD28. PBMC (5×$10^4$ cells/well) from 13 healthy volunteers were cultured in duplicate in 200 µl of complete medium supplemented with the highest solvent concentration ($10^{-6}$ M), and $10^{-6}$ M, $10^{-7}$ M and $10^{-8}$ M of compound 12, in the presence and absence of either LPS (10 µg/ml) or anti-CD3 (12.5 ng/ml)+anti-CD28 (⅓×$10^5$), during 24 hours. Culture supernatants were frozen at −20° C. and IL-8 concentration was quantified by BD FACS Array Bioanalyser by using CBA Flex Set, specific to determine the IL-8 concentration, following the manufacturer instructions.

Figure 7:
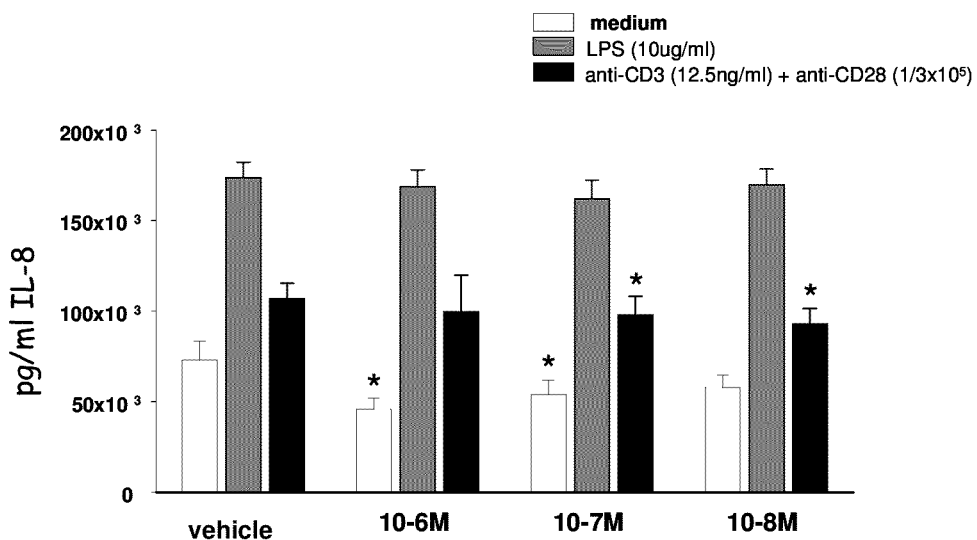
FIG. 7: Influence on IL-8 production in PBMC from healthy volunteers by compound 12. Columns represent the mean and standard error of the duplicate cultures performed in each sample under the different experimental conditions. Asterisks represent statistically significant differences ($p<0.05$) of the corresponding data with respect to the vehicle for each experimental condition.

At concentrations of $10^{-6}$ M y $10^{-7}$ M, the compound 12 significantly inhibited the spontaneous production of IL-8 (p<0.05) (FIG. 7). A significant inhibition of the IL-8 production induced by monoclonal antibodies anti-CD3 and anti-CD28 was observed with compound 12 at a concentration of $10^{-8}$ M. Nevertheless, no effects were observed on the IL-8 production under the LPS stimulation of PBMC.

TABLE 9

TNF-alpha production by patients with rheumatoid arthritis. Results are indicated as mean ± standard error values of the secreted cytokine. Statistically significant results are indicated in bold, with their corresponding p values (data with respect to the vehicle for each experimental condition) included in parenthesis.

| | IFN-gamma production in PMBC from patients with rheumatoid arthritis (pg/mL) | | | |
|---|---|---|---|---|
| n = 8 | vehicle | $10^{-6}$ M | $10^{-7}$ M | $10^{-8}$ M |
| medium | 145.49 ± 28.00 | 193.68 ± 45.00 (0.779) | 203.72 ± 50.00 (0.208) | 235.10 ± 60.00 (0.674) |
| LPS (10 µg/ml) | 461.14 ± 85.00 | 205.26 ± 46.00 (0.484) | 146.50 ± 33.00 (0.208) | 248.73 ± 35.00 (0.889) |
| anti-CD3 (12.5 ng/ml) + anti-CD28 (⅓ × $10^5$) | 8406.18 ± 1000.00 | 5115.27 ± 600.00 (0.05) | 6411.71 ± 700.00 (0.05) | 7122.07 ± 950 (0.017) |

TABLE 10

IL-8 production by healthy volunteers. Results are indicated as mean ± standard error values of the secreted cytokine. Statistically significant results are indicated in bold, with their corresponding p values (data with respect to the vehicle for each experimental condition) included in parenthesis.

| | IL-8 production by PMBC from healthy volunteers (pg/mL) | | | |
|---|---|---|---|---|
| n = 13 | vehicle | $10^{-6}$ M | $10^{-7}$ M | $10^{-8}$ M |
| medium | 72814.17 ± 10647.16 | 45634.31 ± 6311.13 (0.016) | 53732.66 ± 7952.75 (0.006) | 57773.60 ± 6667.57 (0.087) |
| LPS (10 µg/ml) | 173877.36 ± 8474.49 | 168467.15 ± 9656.96 (0.807) | 162075.59 ± 10258.41 (0.249) | 169609.11 ± 9060.90 (0.861) |
| anti-CD3 (12.5 ng/ml) + anti-CD28 (⅓ × $10^5$) | 107008.56 ± 8351.21 | 99779.72 ± 20000 (0.311) | 97968.61 ± 10220.21 (0.055) | 92989.29 ± 8463.47 (0.028) |

The effect on IL-8 production by PBMC from patients with rheumatoid arthritis was also studied. PBMC (5×10⁴ cells per well) from 8 patients with rheumatoid arthritis were cultured in duplicate in 200 µl of complete medium supplemented with the highest solvent concentration ($10^{-6}$ M), and $10^{-6}$ M, $10^{-7}$ M and $10^{-8}$ M of compound 12, in the presence and in the absence of either LPS (10 µg/ml) or anti-CD3 (12.5 ng/ml)+ anti-CD28 (⅓×$10^5$), during 24 hours. Culture supernatants were frozen at −20° C. and IL-8 concentration was quantified by BD FACS Array Bioanalyser by using CBA Flex Set, specific to determine IL-8 concentration, following the manufacturer instructions.

Figure 8:
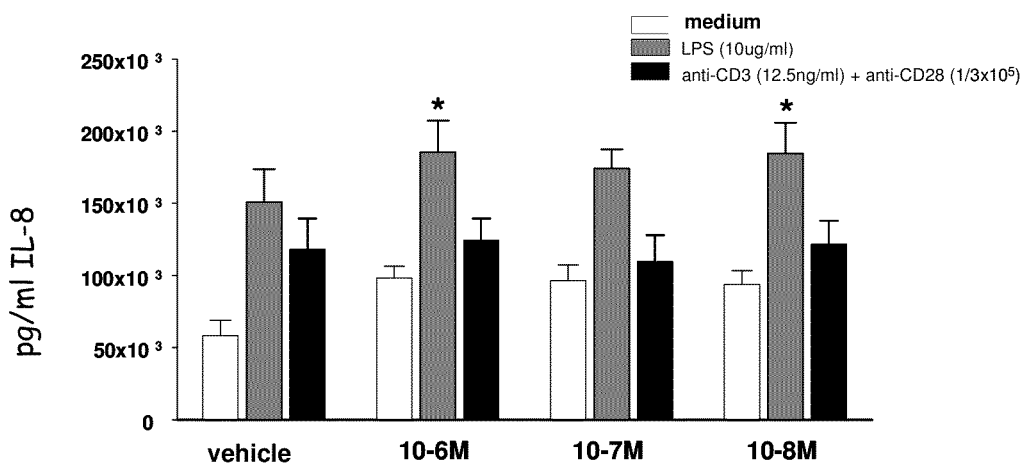
FIG. 8: Influence on IL-8 production in PBMC from patients with rheumatoid arthritis by compound 12. Columns represent the mean and standard error of the duplicate cultures in each sample in the different experimental conditions. Asterisks represent statistically significant differences ($p<0.05$) of the corresponding data with respect to the vehicle for each experimental condition.

The presence of compound 12 in the culture, at concentrations of $10^{-6}$ M and $10^{-8}$ M, significantly inhibited the LPS-induced production of IL-8 in PBMC from patients with rheumatoid arthritis whereas neither modified the spontaneous IL-8 production nor that induced by the combination of monoclonal antibodies anti-CD3 and anti-CD28 (FIG. 8).

ies anti-CD3 and anti-CD28. PBMC (5×10⁴ cells per well) from 13 healthy volunteers were cultured in duplicate 200 µl of complete medium supplemented with the highest solvent concentration ($10^{-6}$ M), and $10^{-6}$ M, $10^{-7}$ M and $10^{-8}$ M of compound 12, in the presence and absence of either LPS (10 µg/ml) or anti-CD3 (12.5 ng/ml), +anti-CD28 (⅓×$10^5$), during 24 hours.

On the other hand, PBMC (5×10⁴ cells per well) from 8 patients with rheumatoid arthritis were cultured in duplicate in 200 µl of complete medium supplemented with the highest solvent concentration ($10^{-6}$ M), and $10^{-6}$ M, $10^{-7}$ M and $10^{-8}$ M of compound 12 in the presence and absence of either LPS (10 µg/ml) or anti-CD3 (12.5 ng/ml), +anti-CD28 (⅓× $10^5$), during 24 hours. Culture supernatants were frozen at −20° C. and IL-10 concentration was assayed by BD FACS Array Bioanalyser by using CBA Flex Set, specific to determine IL-10 concentration, following the manufacturer instructions.

TABLE 11

IL-8 production by patients with rheumatoid arthritis. Results are indicated as mean ± standard error values of the secreted cytokine. Statistically significant results are indicated in bold, with their corresponding p values (data with respect to the vehicle for each experimental condition) included in parenthesis.

| | IL-8 production in PMBC from patients with rheumatoid arthritis (pg/mL) | | | |
|---|---|---|---|---|
| n = 8 | vehicle | $10^{-6}$ M | $10^{-7}$ M | $10^{-8}$ M |
| medium | 57877.64 ± 11143.52 | 98012.08 ± 8395.97 (0.208) | 96498.50 ± 10784.62 (0.161) | 93977.67 ± 9247.38 (0.123) |
| LPS (10 µg/ml) | 150759.65 ± 22966.06 | 185536.78 ± 22000.00 (0.012) | 174156.23 ± 13385.66 (0.208) | 184541.37 ± 21500.00 (0.012) |
| anti-CD3 (12.5 ng/ml) + anti-CD28 (⅓ × $10^5$) | 118017.97 ± 21116.00 | 124576.09 ± 14605.02 (0.263) | 109607.00 ± 18310.15 (0.889) | 121587.88 ± 16117.25 (0.575) |

Example 9

Effects of Compound 12 on Interleukin 10 (IL-10) Production

Figure 9:
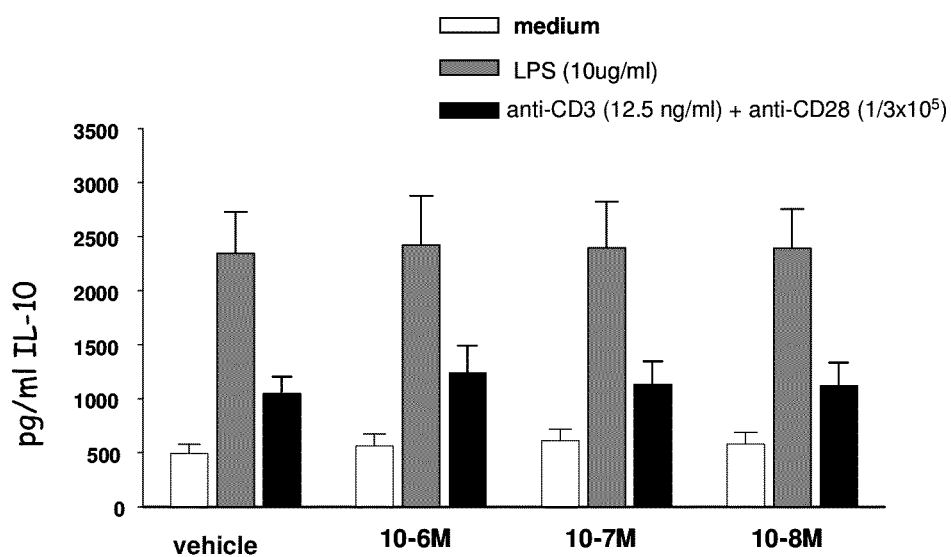
FIG. 9: Influence on IL-10 production in PBMC from healthy volunteers by compound 12. Columns represent the mean and the standard error of the duplicate cultures performed in each sample in the different experimental conditions. No statistical differences were found.
Figure 10:
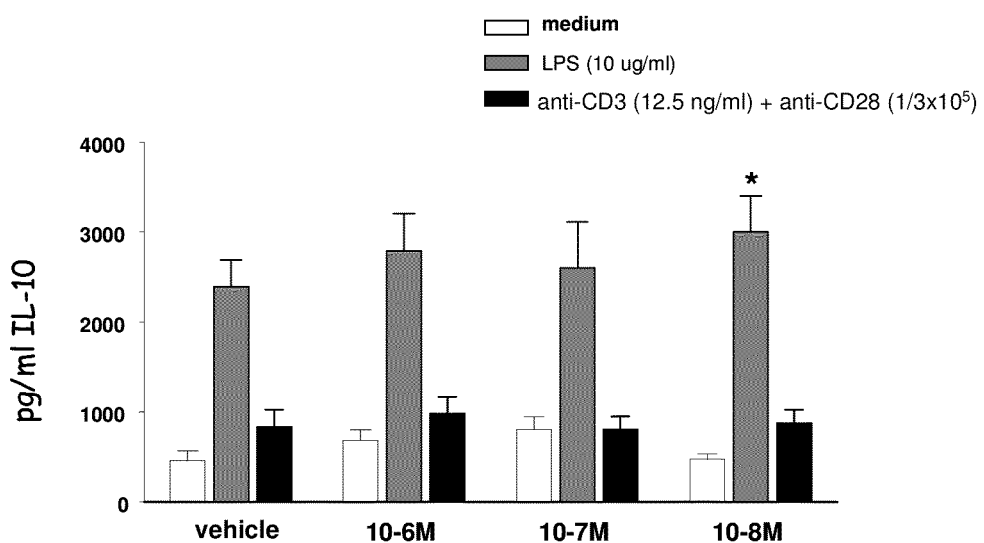
FIG. 10: Influence on IL-10 production in PBMC from patients with rheumatoid arthritis by compound 12. Columns represent the mean and standard error of the duplicate cultures performed in each sample in the different experimental conditions. The asterisk represents the statistically significant differences ($p<0.05$) of the corresponding data with respect to the vehicle.

The effects of compound 12 on IL-10 production by the PBMC from healthy volunteers and patients with rheumatoid arthritis were investigated in the presence and absence of LPS stimulation and with the combination of monoclonal antibod- Compound 12 showed no effects on the IL-10 production by PBMC from healthy volunteers in the presence and in the absence of both studied stimuli (FIGS. 9 y 10). However, the presence of compound 12 in the culture, at a concentration of $10^{-8}$, significantly inhibited IL-10 production after stimulation with LPS (p<0.05). Compound 12 induced no significant effects neither on the spontaneous production of IL-10 nor after the stimulation with monoclonal antibodies anti-CD3 and anti-CD28 by PBMC from patients with rheumatoid arthritis.

TABLE 12

IL-10 production by healthy volunteers. Results are indicated as mean ± standard error values of the secreted cytokine. The corresponding p values (data with respect to the vehicle for each experimental condition) included in parenthesis.

| | IL-10 production by PMBC from healthy volunteers (pg/mL) | | | |
|---|---|---|---|---|
| n = 13 | vehicle | $10^{-6}$ M | $10^{-7}$ M | $10^{-8}$ M |
| medium | 490.46 ± 87.16 | 559.06 ± 112.20 (0.753) | 609.10 ± 108.74 (0.701) | 578.66 ± 106.20 (0.861) |
| LPS (10 µg/ml) | 2342.20 ± 384.02 | 2420.68 ± 455.50 (0.507) | 2392.99 ± 427.86 (0.507) | 2389.63 ± 366.01 (0.701) |
| anti-CD3 (12.5 ng/ml) + anti-CD28 (⅓ × $10^5$) | 1042.64 ± 162.36 | 1239.47 ± 251.24 (0.507) | 1132.69 ± 213.32 (0.382) | 1122.51 ± 211.03 (0.507) |

TABLE 13

IL-10 production by patients with rheumatoid arthritis. Results are indicated as mean ± standard error values of the secreted cytokine. Statistically significant results are indicated in bold, with their corresponding p values (data with respect to the vehicle for each experimental condition) included in parenthesis.

| | IL-10 production in PMBC from patients with rheumatoid arthritis (pg/mL) | | | |
|---|---|---|---|---|
| n = 8 | vehicle | $10^{-6}$ M | $10^{-7}$ M | $10^{-8}$ M |
| medium | 452.69 ± 107.47 | 682.50 ± 113.65 (0.674) | 798.92 ± 144.46 (0.401) | 468.14 ± 65.80 (0.263) |
| LPS (10 µg/ml) | 2388.64 ± 300.00 | 2787.12 ± 416.91 (0.069) | 2597.85 ± 513.19 (0.327) | 3000.00 ± 400.00 (0.025) |
| anti-CD3 (12.5 ng/ml) + anti-CD28 (⅓ × $10^5$) | 836.39 ± 189.09 | 976.96 ± 187.99 (0.484) | 805.41 ± 141.23 (1.000) | 872.06 ± 150.87 (0.674) |

Other Effects of Compound 12 on Immune System Cells.

Example 10

Effect of Compound 12 on the Proliferative Response of PBMC

The effect of compound 12 on the proliferative response of PBMC from healthy volunteers was investigated in the presence and in the absence of stimulation with phytohaemaglutinin (PHA) 10 µg/ml; PHA 2 µg/ml plus exogenous IL-2 supplementation (25 IU/ml), and a combination of monoclonal antibodies anti-CD3 (12.5 ng/ml) and anti-CD28 (1:320.000).

PBMC was cultured during 4 days (50.000 cells per well) at 37° C. and 5% $CO_2$ atmosphere (Cell incubator HERA Cell 150, Thermoscientific, Thermoelectron, 63505 Lagenselbold, GE) in complete culture medium. Culture stimulation conditions were the absence or presence or phytohaemaglutinin (PHA Sigma Ref #L-8902, Madrid, Spain), 10 µg/ml; PHA 2 µg/ml with exogenous IL-2 supplementation (25 IU/ml, Human recombinant IL-2, Macrolin, Chiron Ibérica, batch #SA753228/4, Madrid, Spain) and monoclonal antibodies anti-CD3 (12.5 ng/ml)+anti-CD28 (1:320.000). Methyl-3H-Thymidine was added (American Radiochemical 60 Ci/mmol methyl-$^3$H-Thymidine, ITISA, Madrid, Spain) during the last 8 hours of culture. Cells were harvested in glass fibre membranes and embebed in scintillation medium (1450-441 Meltilex A, de Wallac Oy, Ref#1450-441). The DNA-incorporated radioactive was quantified by using a betha particles counter Wallac Oy. As a control of the cellular viability of the cultures, these were observed at the microscope (Zeiss Axiovert 40CFL, Karl Zeiss Microimagen GmbH, Göttingen, Germany) regarding the density and morphology of the cell cultures in the presence of medium, with no other signals, in order to detect and quantify possible mitogenic direct actions of the study molecules on the PBMC, and the cellular viability after incubation was assessed.

Figure 11:
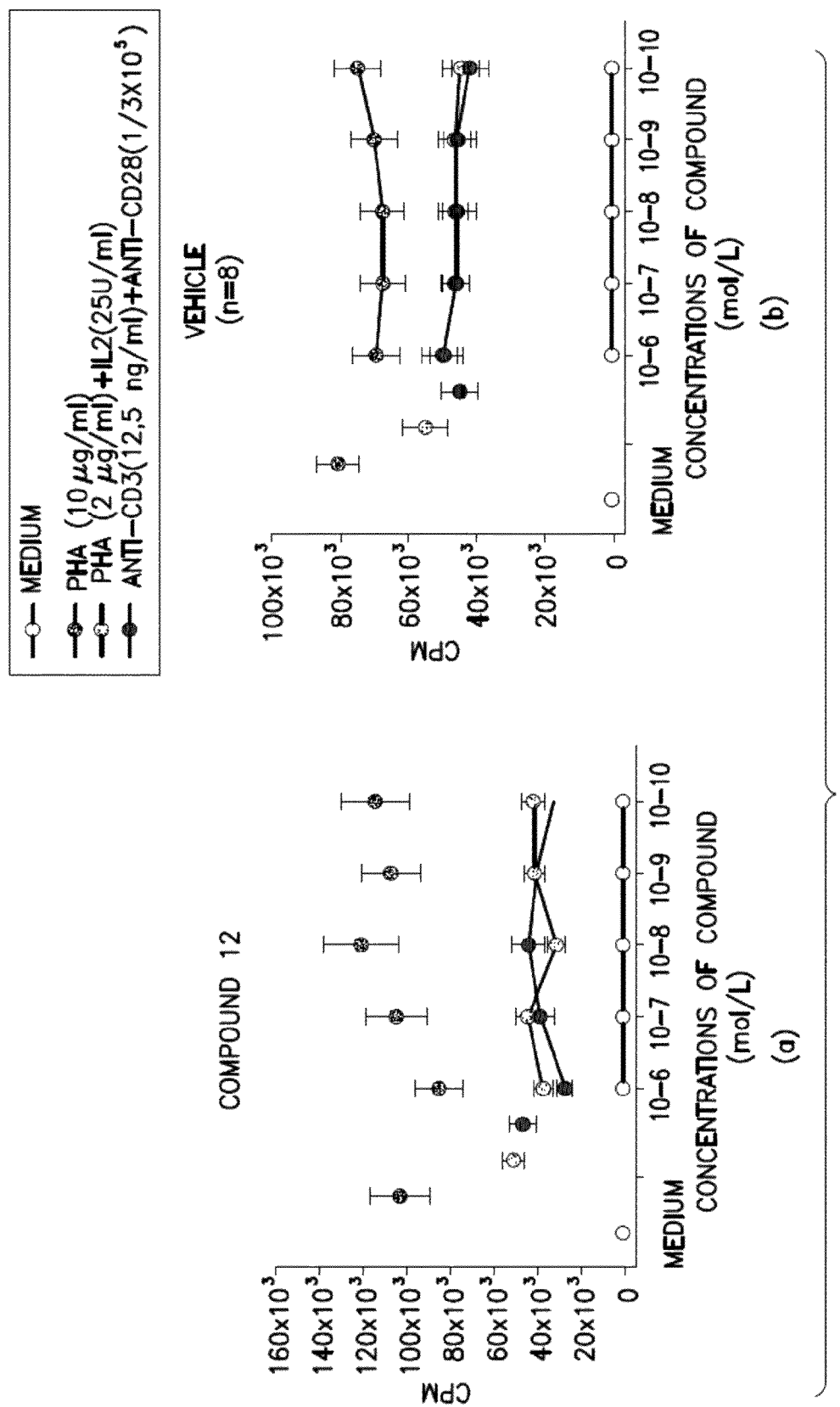
FIG. 11: Effect of compound 12 (a) and vehicle (b) on the proliferative response of PBMC from healthy volunteers in the presence and in the absence of stimulation with either PHA, PHA plus IL-2, or a combination of monoclonal antibodies anti-CD3 (T3) and anti-CD28.

The presence of compound 12 in the culture did not significantly modify the proliferative response of the PBMC from healthy volunteers in the absence and in the presence of the various mitogenic stimuli studied (FIGS. 11a and 11b).

Example 11

Effect of Compound 12 on the Shedding of CD62L by PBMC

The effect of compound 12 on the shedding of CD62L in lymphocytes and monocytes of PBMC from healthy volunteers was investigated.

Figure 12:
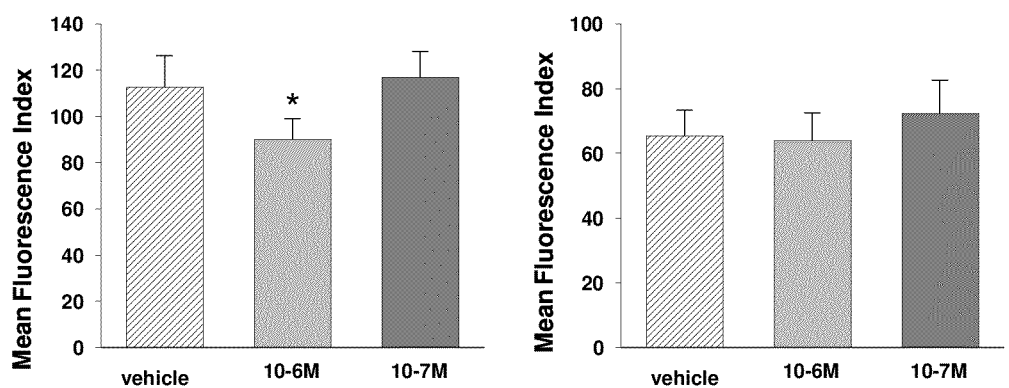
FIG. 12: Effect of compound 12 on the shedding of CD62L in lymphocytes (a) and monocytes (b) of PBMC from healthy volunteers.

In the presence of compound 12 at a concentration of $10^{-6}$ M, the CD62L shedding (CD62L—Phycoerithryn (PE), don BD SK11 Cat No. 341012, BD Biosciences) increases significantly (p<0.05). Notably, this decrease in the mean fluorescence intensity of CD62L-PE labelling detected after the shedding of CD62L, selectively occurred in lymphocytes but significant differences were not observed in monocytes (FIGS. 12a and 12b).

TABLE 14

Mean fluorescence intensity of surface CD62L expression in lymphocytes

| n = 10 | lymphocytes | | |
|---|---|---|---|
| | vehicle | $10^{-6}$ M | $10^{-7}$ M |
| Geometric mean | 112.68 | 90.01 | 116.90 |
| Standard error | 13.57 | 8.93 | 11.02 |

TABLE 15

Mean fluorescence intensity of surface CD62L expression in monocytes

| n = 10 | monocytes | | |
|---|---|---|---|
| | vehicle | $10^{-6}$ M | $10^{-7}$ M |
| Geometric mean | 65.34 | 63.90 | 72.30 |
| Standard error | 8.06 | 8.52 | 10.21 |

TABLE 16 p values (data with respect to the vehicle for each experimental condition)

| n = 10 | $10^{-6}$ | $10^{-7}$ |
|---|---|---|
| lymphocytes | 0.047 | 0.333 |
| monocytes | 0.721 | 0.878 |

What is claimed is:

1. A method for the treatment of rheumatoid arthritis, hepatitis, or insulinitis, comprising administering to a subject in need thereof a therapeutically effective amount of a compound selected from the group consisting of:

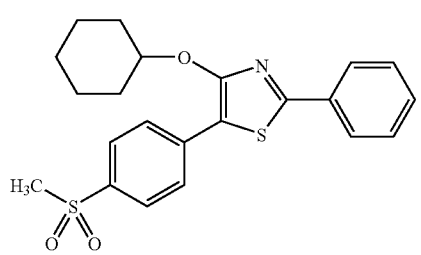
(1)

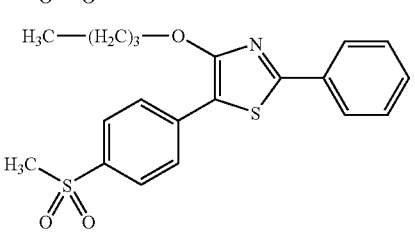
(2)

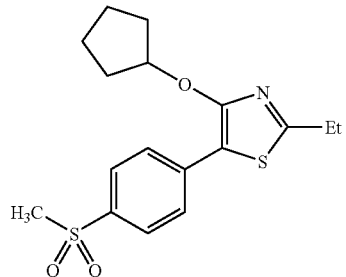
(3)

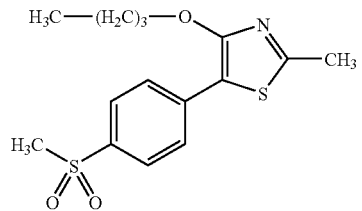
(4)

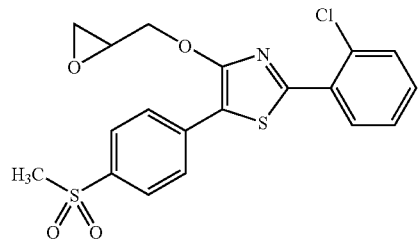
(5)

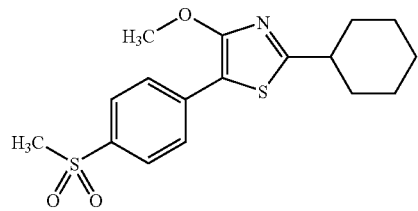
(6)

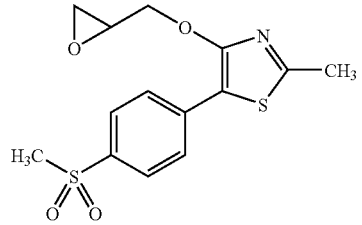
(7)

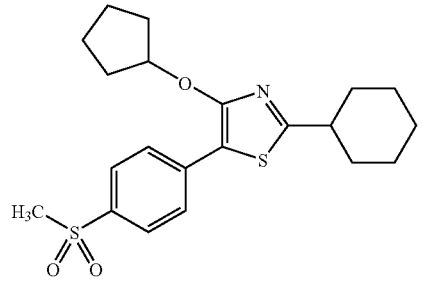
(8)

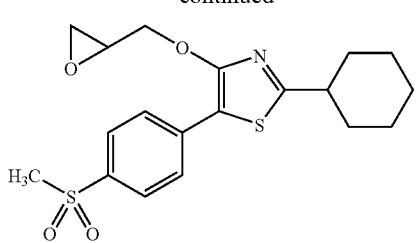
(9)
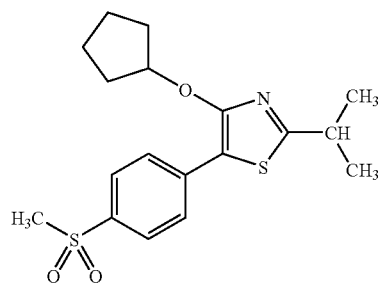
(10)
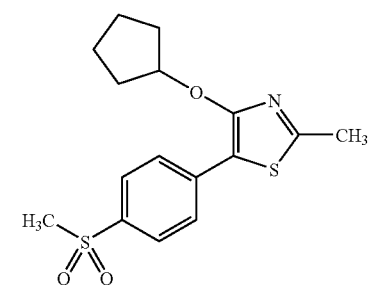
(12)
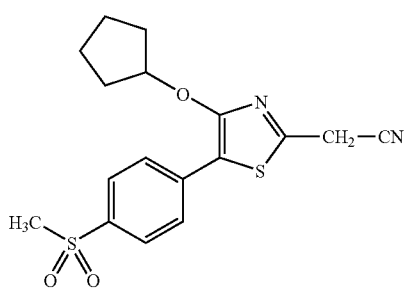
(13)
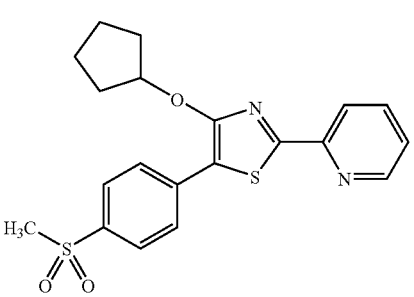
(14)
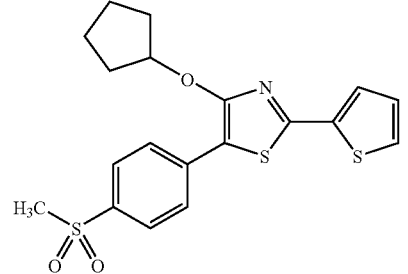
(15)
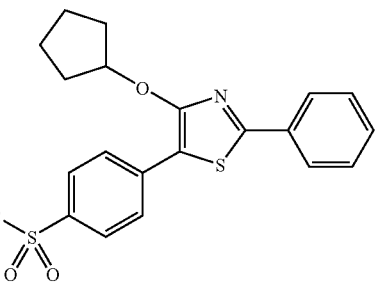
(16)
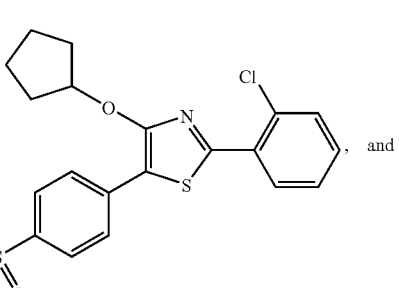
(17)
, and
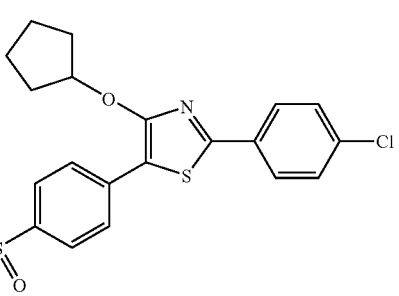
(18)
or a pharmaceutically acceptable salt thereof.
2. A method for the treatment of rheumatoid arthritis, comprising administering to a subject in need thereof a therapeutically effective amount of a compound selected from the group consisting of:
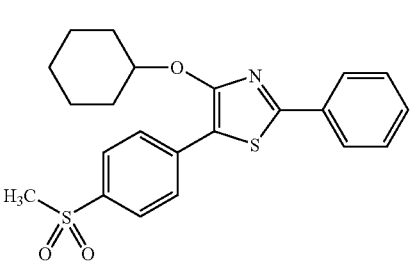
(1)
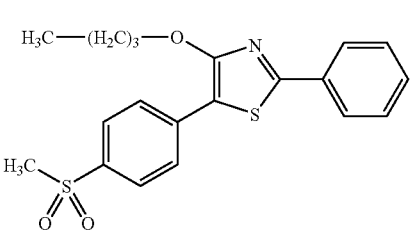
(2)

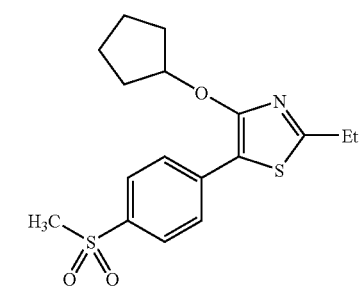
(3)
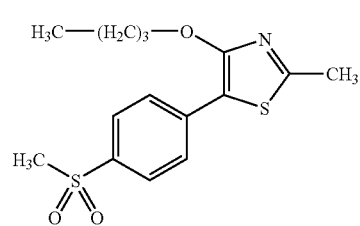
(4)
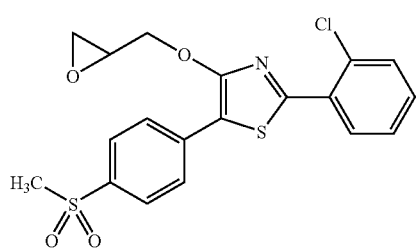
(5)
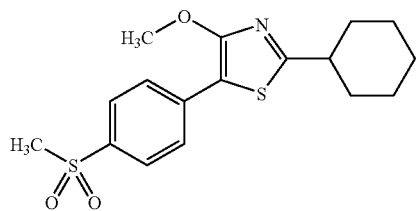
(6)
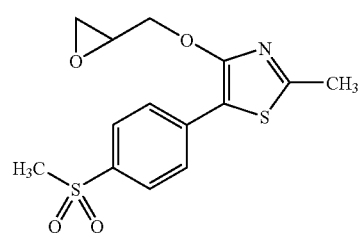
(7)
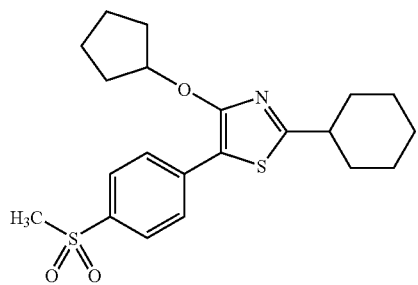
(8)
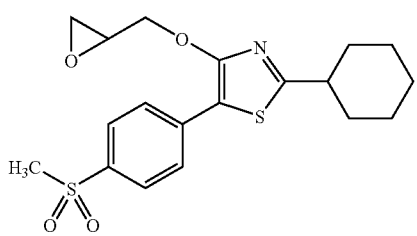
(9)
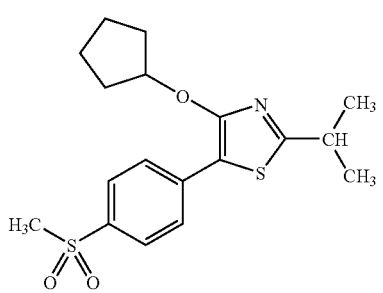
(10)
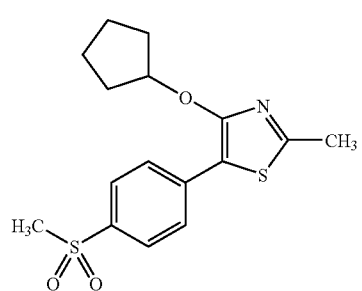
(12)
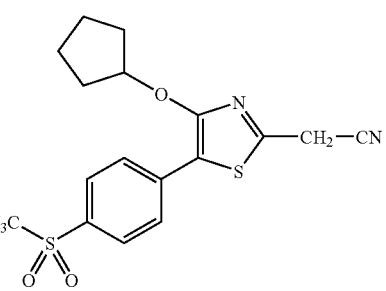
(13)
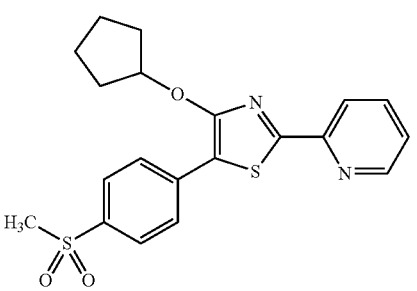
(14)

-continued
(15)
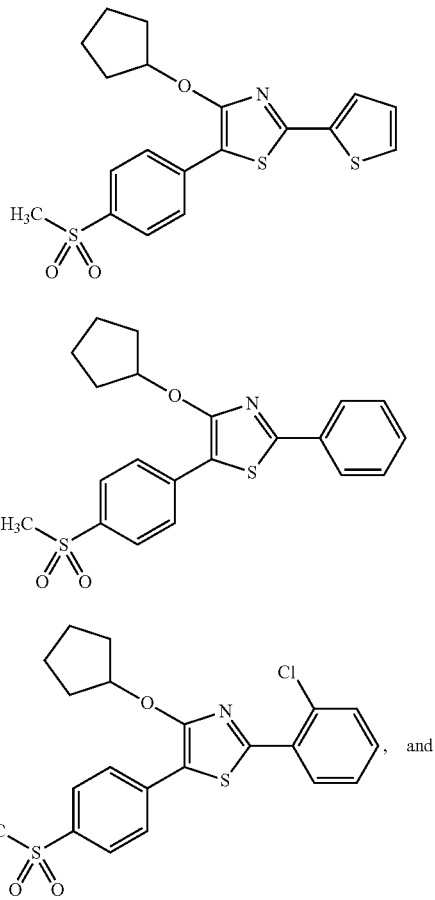
(16)
(17)
(18)
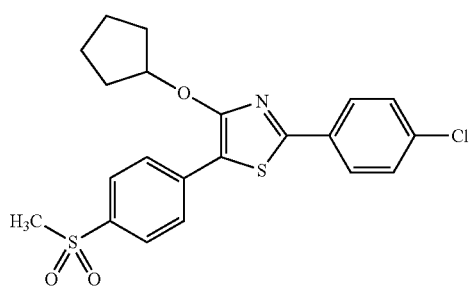
or a pharmaceutically acceptable salt thereof.
3. The method of claim 2, wherein the compound is
(12)
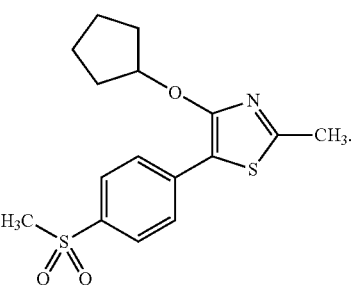
4. The method of claim 1, for the treatment of hepatitis.
5. The method of claim 4, wherein the compound is
(12)
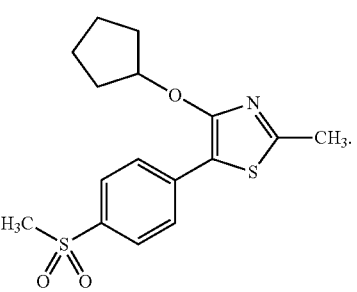
6. The method of claim 1, for the treatment of insulinitis.
7. The method of claim 6, wherein the compound is
(12)
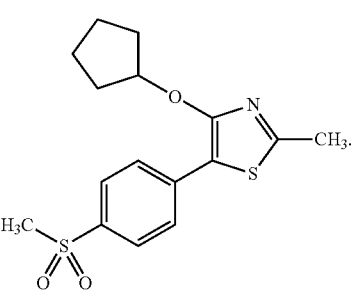
* * * * *

UNITED STATES PATENT AND TRADEMARK OFFICE
CERTIFICATE OF CORRECTION

PATENT NO. : 8,492,411 B2 Page 1 of 1
APPLICATION NO. : 12/838439
DATED : July 23, 2013
INVENTOR(S) : Victor Rubio Royo et al.

It is certified that error appears in the above-identified patent and that said Letters Patent is hereby corrected as shown below:

In the Specification

At column 27, Table 6:
    in the second to last row of the column titled "$10^{-6}M$", the value "34.21 ± 63.00"
should be
    -- 334.21 ± 63.00 --

At column 34, line 61:
    "...(CD62L-Phycoerithryn (PE), don..."
should be
    -- ...(CD62L-Phycoerithryn (PE), clon... --

Signed and Sealed this
Twenty-fourth Day of September, 2013

Teresa Stanek Rea
*Deputy Director of the United States Patent and Trademark Office*